US012416549B2

(12) United States Patent
Nishi et al.

(10) Patent No.: US 12,416,549 B2
(45) Date of Patent: Sep. 16, 2025

(54) LIQUID COLLECTOR

(71) Applicant: PROVIGATE INC., Tokyo (JP)

(72) Inventors: Mitsumi Nishi, Tokyo (JP); Noriko Miyauchi, Tokyo (JP)

(73) Assignee: PROVIGATE INC., Tokyo (JP)

( * ) Notice: Subject to any disclaimer, the term of this patent is extended or adjusted under 35 U.S.C. 154(b) by 489 days.

(21) Appl. No.: 18/000,335

(22) PCT Filed: May 30, 2021

(86) PCT No.: PCT/JP2021/020577
§ 371 (c)(1),
(2) Date: Nov. 30, 2022

(87) PCT Pub. No.: WO2021/246348
PCT Pub. Date: Dec. 9, 2021

(65) Prior Publication Data
US 2023/0221216 A1     Jul. 13, 2023

(30) Foreign Application Priority Data

Jun. 1, 2020   (JP) .................................. 2020-095795

(51) Int. Cl.
*G01N 1/10*   (2006.01)
*A61B 10/00*   (2006.01)
*G01N 1/02*   (2006.01)

(52) U.S. Cl.
CPC ........ *G01N 1/10* (2013.01); *A61B 2010/0067* (2013.01); *G01N 2001/028* (2013.01)

(58) Field of Classification Search
CPC .. G01N 1/02; G01N 1/10; G01N 1/14; G01N 2001/149; G01N 2001/1031; G01N 2001/1056; G01N 2001/028; B01L 3/50
(Continued)

(56) References Cited

U.S. PATENT DOCUMENTS

2002/0127580 A1*  9/2002  Quay ................. A61B 5/14546
435/6.14
2002/0146346 A1   10/2002 Konecke
(Continued)

FOREIGN PATENT DOCUMENTS

JP       2010266203 A    11/2010
JP        6104440 B1     3/2017
(Continued)

OTHER PUBLICATIONS

Supplemental European Search Report., EP Application No. 21817513, completed Apr. 25, 2024, Examiner Nina Jansson Godoy Apr. 25, 2024.
(Continued)

*Primary Examiner* — Nathaniel J Kolb
(74) *Attorney, Agent, or Firm* — McBee, Moore & Vanik IP, LLC

(57) ABSTRACT

An embodiment of the present disclosure provides a liquid collector that collects liquid, the liquid collector including: a flow passage member including a flow passage that connects one end and other end of the flow passage member; a contact member that is disposed at the one end of the flow passage member, that includes an elastic material, and that is configured to come into contact with a target from which liquid is to be collected; and a container that receives the liquid discharged from the flow passage at the other end of the flow passage member.

18 Claims, 14 Drawing Sheets

(58) Field of Classification Search
USPC .......................................... 73/864.51, 864.72
See application file for complete search history.

(56) References Cited

U.S. PATENT DOCUMENTS

| | | | |
|---|---|---|---|
| 2011/0146419 A1* | 6/2011 | Gonzalez | A61B 10/0045 |
| | | | 73/864.11 |
| 2011/0224579 A1* | 9/2011 | Maas | G01N 1/02 |
| | | | 600/573 |
| 2016/0022189 A1 | 1/2016 | Pouteau et al. | |
| 2016/0302776 A1* | 10/2016 | Adolphson | A61B 10/0096 |
| 2016/0349153 A1* | 12/2016 | Mao | A61B 5/151 |
| 2019/0021704 A1* | 1/2019 | Shastry | G01N 33/948 |
| 2019/0159710 A1* | 5/2019 | Iwasawa | A61B 5/150343 |

FOREIGN PATENT DOCUMENTS

| | | |
|---|---|---|
| JP | 2017507730 A | 3/2017 |
| JP | 2018511061 A | 4/2018 |
| JP | 2020503497 A | 1/2020 |

OTHER PUBLICATIONS

PCT International Search Report for PCT/JP2021/020577, mailed Aug. 17, 2021, with English translation, 5 pages.

\* cited by examiner

LIQUID COLLECTOR

CROSS-REFERENCE TO RELATED APPLICATIONS

This application is the National Stage entry of International Application No. PCT/JP2021/020577, filed 30 May 2021, which claims priority to Japanese Application No. 2020-095795, filed 1 Jun. 2020.

BACKGROUND

Technical Field

The present disclosure relates to a liquid collector.

Description of Related Art

A small amount of liquid may be collected by, for example, suction using a dropper or a syringe or absorption into test paper.

It is desirable to collect liquid efficiently. However, when, for example, a small amount of liquid is collected by using a dropper or the like, it may be difficult to efficiently collect all of the liquid.

Summary of Invention

Here, it is recognized, for example, without limitation, that efficient collection of liquid is desired.

SUMMARY

Some embodiments of the present disclosure provide a liquid collector. In some embodiments, the liquid collector collects liquid. In some embodiments, the liquid collector includes a flow passage member. In some embodiments, the flow passage member includes a flow passage that connects one end and other end of the flow passage member. In some embodiments, the liquid collector includes a contact member. In some embodiments, the contact member is disposed at the one end of the flow passage member. In some embodiments, the contact member includes an elastic material. In some embodiments, the contact member is configured to come into contact with a target from which liquid is to be collected. In some embodiments, the liquid collector includes a container. In some embodiments, the container receives the liquid discharged from the flow passage at the other end of the flow passage member.

Some embodiments of the present disclosure provide a liquid collector. In some embodiments, the liquid collector collects liquid. In some embodiments, the liquid collector includes a flow passage member. In some embodiments, the flow passage member includes a plurality of flow passages that connect one end and other end of the flow passage member. In some embodiments, the liquid collector includes a container. In some embodiments, the container receives the liquid discharged from the flow passages at the other end of the flow passage member.

According to the above-described embodiments, for example, the liquid can be efficiently collected.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

DESCRIPTION OF EMBODIMENTS

Figure 1:
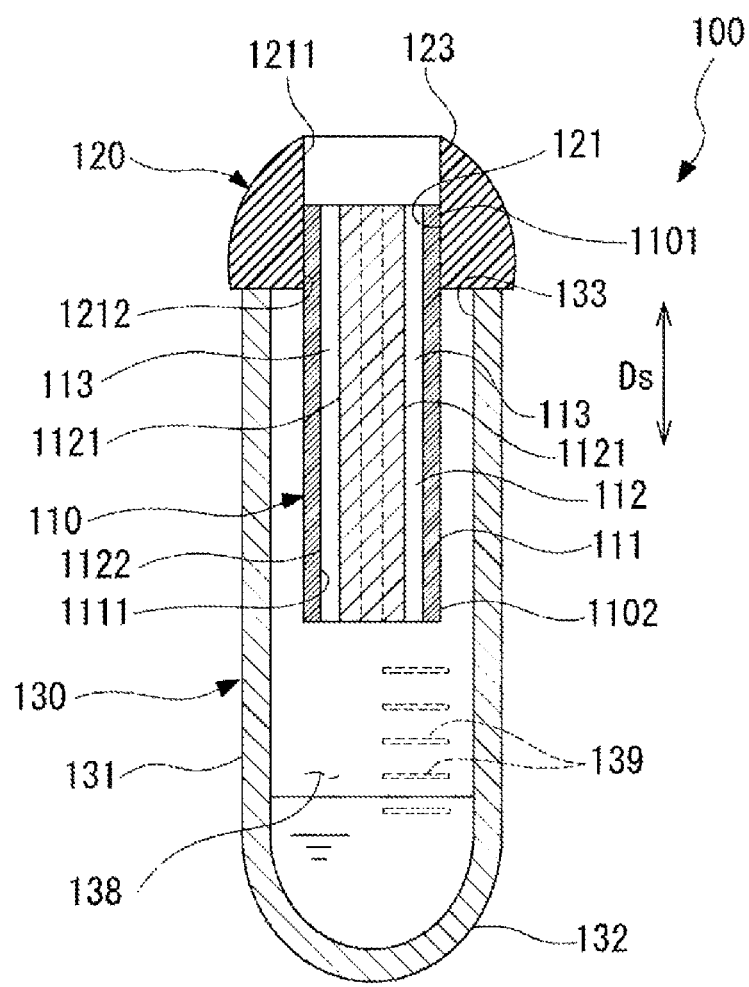
FIG. 1 is a sectional view of a liquid collector according to an embodiment.

In some embodiments, a liquid collector collects liquid (sometimes also referred to as solution).

In some embodiments, the liquid may be body fluid produced by secretion in a target subject, or liquid other than body fluid. The liquid other than body fluid may be liquid adhering to a target object or liquid not adhering to a target object. The liquid not adhering to a target object may be liquid contained in a target object.

The liquid to be collected may be a solution. The liquid may be body fluid, a solution derived from body fluid, or diluted body fluid. The liquid may be a solution other than (not derived from) body fluid, or a mixture of body fluid or a solution derived from body fluid with a solution not derived from body fluid. The solution may be a solution used for sample measurement or a solution used for calibration measurement. For example, the solution may be a standard solution or a calibration solution. The sample to be measured may be a specimen.

Examples of the body fluid include lymph fluid, tissue fluid such as inter-tissue fluid, intercellular fluid, and interstitial fluid, coelomic fluid, serous cavity fluid, pleural fluid, ascites fluid, pericardial fluid, cerebrospinal fluid, synovial fluid, and aqueous humor. Examples of the body fluid further include digestive juice, such as saliva, gastric juice, bile, pancreatic juice, and intestinal juice, sweat, tear, nasal mucus, urine, semen, vaginal fluid, amniotic fluid, and milk. The body fluid may be body fluid of an animal or a human. The "body fluid" may be a solution. The solution may include a physiological buffer, such as phosphate-buffered saline (PBS) or N-tris(hydroxymethyl)methyl-2-aminoethanesulfonic acid (TES) buffer, containing a measurement target substance. The solution is not particularly limited as long as the measurement target substance is contained.

In some embodiments, the target subject may include, or may be, a human. In some embodiments, the target subject may include, or may be, a non-human animal. The non-human animal may include, or may be, a mammal. Examples of non-human animals include, but are not limited to, working animals, livestock animals, pet animals, and wild animals.

In some embodiments, the liquid collector includes a flow passage member. In some embodiments, the flow passage member may include a flow passage that connects one end and other end of the flow passage member. In some embodiments, the flow passage member may include a plurality of flow passages or only one flow passage. In some embodiments, when the flow passage member includes a plurality of flow passages, the flow passages extend in a pipe axis direction connecting the one end and the other end of the flow passage member. In some embodiments, the flow passages may or may not be substantially parallel to each other.

The term "pipe axis direction" used in this specification means a direction connecting the one end and the other end of the flow passage member.

In some embodiments, the flow passage member may have a columnar shape that extends in the pipe axis direction connecting the one end and the other end of the flow passage member. In some embodiments, the flow passage member having the columnar shape may have a plurality of grooves or only one groove that extends in the pipe axis direction along an outer peripheral surface of the flow passage member. In some embodiments, the groove or grooves each serves as a flow passage for the liquid. The cross-sectional shape of the groove or grooves may be, for example, without limitation, a U-shape (the corners may be substantially right angled, obtuse angled, acute angled, or rounded), a V-shape (the corner may be substantially acute angled or rounded), or a general trough shape. In some embodiments, the groove or grooves may extend straight in the pipe axis direction. In some embodiments, the groove or grooves may not extend straight in the pipe axis direction. For example, the groove or grooves may be formed in the flow passage member in a helical shape. For example, the groove or grooves may be inclined with respect to the pipe axis direction at the one end at which the liquid is absorbed.

In some embodiments, the flow passage member may include an outside tube. In some embodiments, the outside tube may have a tubular shape that extends in the pipe axis direction. In some embodiments, the flow passage member may include an inside member. In some embodiments, the inside member may be inserted in the outside tube. In some embodiments, the inside member may have a plurality of grooves that extend in the pipe axis direction along an outer peripheral surface of the inside member. In some embodiments, an inner peripheral surface of the outside tube and the grooves in the inside member may define the flow passages. In some embodiments, the outside tube may cover at least a portion of the inside member in the pipe axis direction. In some embodiments, the outside tube may cover the entirety of the inside member in the pipe axis direction. In some embodiments, the outside tube may cover a portion of the inside member in the pipe axis direction.

In some embodiments, the flow passage member may have a columnar shape that extends in the pipe axis direction. In some embodiments, the flow passage member having the columnar shape may have a circular shape or an elliptical shape in cross-section when viewed in the pipe axis direction. In some embodiments, the flow passage member may have, for example, a polygonal shape, such as a triangular shape, a quadrangular shape, a pentagonal shape, a hexagonal shape, or an octagonal shape in cross-section. In some embodiments, the flow passage member may have a plurality of flow passages extending therethrough in the pipe axis direction to provide communication between the one end and the other end of the flow passage member. In some embodiments, the flow passage member may have a uniform cross-sectional shape in the pipe axis direction (for example, a cylindrical shape) or a cross-sectional shape that varies in the pipe axis direction (for example, decreases in size toward the one end).

In some embodiments, the flow passage member may be formed by bundling a plurality of single pipes that extend in the pipe axis direction. In some embodiments, each single pipe may have a tubular shape that extends in the pipe axis direction and include a flow passage that connects one end and the other end of the single pipe. In some embodiments, the single pipes may be joined together by adhesion or fusion bonding. In some embodiments, the single pipes may be bundled together with a band or the like. In some embodiments, the single pipes may be formed integrally with each other by using a resin material. When, for example, the single pipes are bundled together, holes in the single pipes and gaps between the single pipes serve as flow passages for the liquid.

In some embodiments, the flow passage member may include a porous material. The porous material may be, for example, without limitation, a porous ceramic or a sponge. The porous material may serve as a flow passage that allows fluid to flow therethrough by capillarity.

In some embodiments, the flow passage member may include an outer tube. In some embodiments, the outer tube may have a tubular shape that extends in the pipe axis direction. In some embodiments, the flow passage member may include a plurality of inner pipes. In some embodiments, the inner pipes may be inserted in the outer tube. In some embodiments, the inner pipes may extend in the pipe axis direction. When, for example, the inner pipes are disposed in the outer tube, holes formed in the inner pipes, gaps between the inner pipes, and gaps between an inner peripheral surface of the outer tube and the inner pipes disposed inside the inner peripheral surface serve as flow passages for fluid.

In some embodiments, the liquid collector includes a contact member. In some embodiments, the contact member may be disposed at the one end of the flow passage member. In some embodiments, the contact member may be configured to come into contact with a target from which the liquid is to be collected. In some embodiments, the contact member may include, or may be, an elastic material. In some embodiments, when the contact member includes an elastic material, the contact member may be a combination of a portion made of the elastic material and a portion made of another material. In some embodiments, the contact member may have mechanical, physical, chemical, and biological characteristics, such as elasticity and surface shape, such that the contact member can be brought into contact with, for example, a skin, a mucous membrane, or an eyeball of an animal, such as a human, substantially without causing damage thereto. In some embodiments, the elastic material that forms the contact member may be softer than the flow passage member.

The term "elastic material" used in this specification generally refers to a material that is elastically deformable when the contact member is pressed against a target subject or a target object. The elastic material can be brought into contact with a target subject or a target object substantially without causing damage to a surface thereof in normal use. In some embodiments, the elastic material may include a material such as a silicone-based material, an urethane-based material (foam type, low-rebound material), a rubber material, a synthetic resin material (e.g., polyethylene), or a combination thereof (for example, without limitation, a structure including an inner portion made of low-rebound urethane and an outer portion made of silicone), or be formed mainly of a material that is one of, or a combination of, the above-mentioned materials.

In some embodiments, the contact member may include, or be made of, a hydrophilic material. In some embodiments, a contact surface may be hydrophilic. The contact member may have a hydrophilized surface. In some embodiments, the contact surface may be hydrophobic or water repellent. In some embodiments, the contact surface may be rough. In such a case, for example, a user (target subject) may recognize that the contact surface is in contact with their skin. In some embodiments, the contact surface may be embossed.

In some embodiments, the contact member may include an inlet opening. In some embodiments, the inlet opening may come into contact with a surface of the target from which the liquid is to be collected and allow introduction of the liquid that is on or near the surface. In some embodiments, the contact member may include an outlet opening. In some embodiments, the outlet opening may be connected to the inlet opening to provide fluid communication. In some embodiments, the outlet opening may be connected to the flow passage member to provide fluid communication. In some embodiments, the one end of the flow passage member may be fitted to the outlet opening in the contact member. In some embodiments, the contact member may include a sleeve. In some embodiments, the sleeve may have a tubular shape that extends toward the other end of the flow passage member. When, for example, the contact member includes the sleeve having a tubular shape that extends toward the other end of the flow passage member, the flow passage member is fitted to and covered with the sleeve. In some embodiments, the inlet opening and the outlet opening may have the same size or shape. In some embodiments, the inlet opening and the outlet opening may have different sizes or shapes. For example, the inlet opening may be relatively wide, and the thickness of a flow passage that provides fluid communication between the inlet opening and the outlet opening may be reduced toward the outlet opening. This arrangement may be reversed.

In some embodiments, the contact member may have a contact surface in a region around the inlet opening. In some embodiments, the contact surface may come into contact with a surface of the target from which the liquid is to be collected. In some embodiments, the contact surface may protrude from the one end of the flow passage member. In some embodiments, at least a portion of the contact surface may be spherical, or the entirety of the contact surface may be spherical.

In some embodiments, the liquid collector includes a container. In some embodiments, the container may receive the liquid discharged from the flow passage or flow passages at the other end of the flow passage member. In some embodiments, the container may include a peripheral wall having a tubular shape. In some embodiments, the peripheral wall may extend in the pipe axis direction. In some embodiments, the container may include a bottom portion. In some embodiments, the bottom portion may block the peripheral wall at one side in the pipe axis direction. For example, the container may be formed of the peripheral wall and the bottom portion so as to have a tubular shape with a bottom. In some embodiments, the bottom portion of the container may be spaced from the other end of the flow passage member in the pipe axis direction. In some embodiments, a reservoir space that stores the liquid may be defined between the bottom portion of the container and the other end of the flow passage member. In some embodiments, the container may have a shape of a dish, a bowl, a tray, etc., having a recess capable of receiving the liquid.

In some embodiments, the container may have an opening at a side opposite to the side at which the bottom portion is provided in the pipe axis direction. In some embodiments, the contact member may be disposed to close the opening of the container. In some embodiments, the contact member may be mechanically connected to the opening of the container to close the opening of the container. In some embodiments, the contact member may be placed on the opening of the container to close the opening of the container without being mechanically connected to the opening of the container.

In some embodiments, the peripheral wall of the container may have an inner diameter that gradually decreases toward the bottom portion in the pipe axis direction. In some embodiments, the other end of the flow passage member may be in contact with an inner peripheral surface of the peripheral wall of the container. When, for example, the other end of the flow passage member is in contact with the inner peripheral surface of the peripheral wall, the liquid in the flow passage or flow passages of the flow passage member easily moves to the inner peripheral surface of the peripheral wall.

In some embodiments, the container may or may not have an air hole that provides communication with the outside of the container. In some embodiments, the air hole may be a through hole connecting the inside and the outside of the container, or a gap between the container and the contact member. In the case where, for example, the container has the air hole, an amount of air corresponding to the volume of the liquid that flows into the container is discharged to the outside of the container through the air hole when the liquid flows into the container through the flow passage or flow passages. In the case where, for example, the container has no air hole, an amount of air corresponding to the volume of the liquid that flows into the container is discharged to the outside of the container through one or more of the flow passages when the liquid flows into the container through the flow passages.

In some embodiments, the air hole may be formed at a position such that the liquid that flows into the container does not flow out of the container when the liquid collector is used. In some embodiments, the air hole may be sealable. For example, a plug or seal that closes the air hole from the outside of the container may be provided. The air hole may be closed to seal the inside of the container. Accordingly, for example, without limitation, the liquid collected in the container can be prevented from leaking to the outside.

In some embodiments, the container may have a scale mark that indicates an amount of the liquid received in the container. When, for example, the container has the scale mark, the amount of the liquid received in the container can be easily visually recognized. In some embodiments, the scale mark may be disposed to enable estimation of the amount of the liquid received in the container. In some embodiments, the scale mark may be disposed at a position corresponding to a predetermined amount (required amount). Accordingly, for example, it can be determined whether a sufficient amount of liquid is collected. One, two, or more scale marks may be provided.

In some embodiments, the container may include a cone-shaped portion. In some embodiments, the cone-shaped portion may be disposed in the container. In some embodiments, at least a portion of the cone-shaped portion in the pipe axis direction may have an inner diameter that gradually decreases toward the bottom portion in the pipe axis direction. In some embodiments, the cone-shaped portion may be formed over at least a partial region in the pipe axis direction, or over the entire region in the pipe axis direction. In some embodiments, the cone-shaped portion may be a component separate from the container or a part of the container. In some embodiments, when the cone-shaped portion is provided, the container may include no bottom portion and be open. In some embodiments, the other end of the flow passage member may be in contact with an inner peripheral surface of the cone-shaped portion. When, for example, when the other end of the flow passage member is in contact with the inner peripheral surface of the cone-shaped portion, the liquid in the flow passage or flow passages of the flow passage member easily moves to the inner peripheral surface of the cone-shaped portion. For example, when the other end of the flow passage member is in contact with the inner peripheral surface of the cone-shaped portion, movement of the flow passage member toward the bottom portion of the container is restricted, and the flow passage member is positioned with respect to the container in the pipe axis direction.

In some embodiments, the liquid collector may include a flow passage member and a container. In some embodiments, the flow passage member may include a plurality of flow passages that connect one end and other end of the flow passage member. In some embodiments, the container may receive liquid discharged from the flow passages at the other end of the flow passage member.

Figure 2:
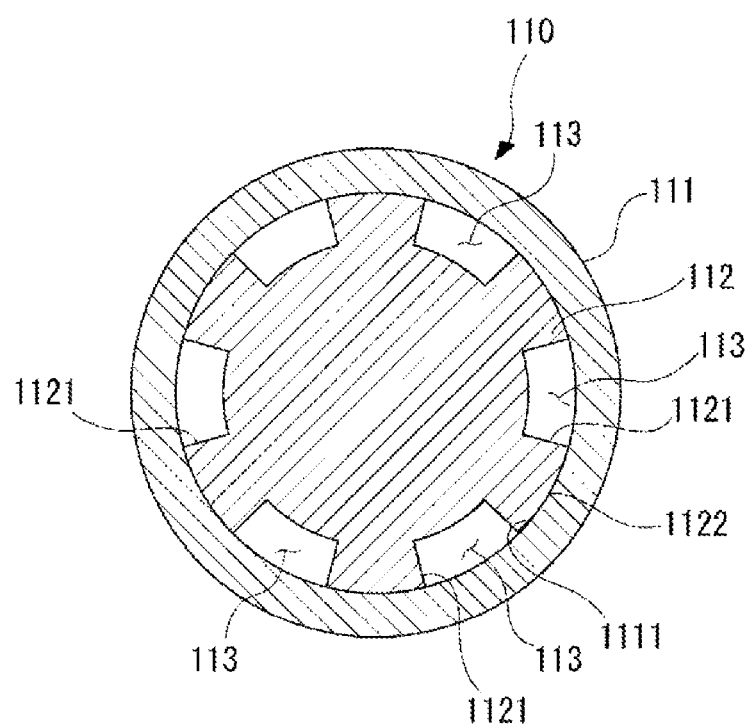
FIG. 2 is a sectional view of a flow passage member of the liquid collector illustrated in FIG. 1.
Figure 3:
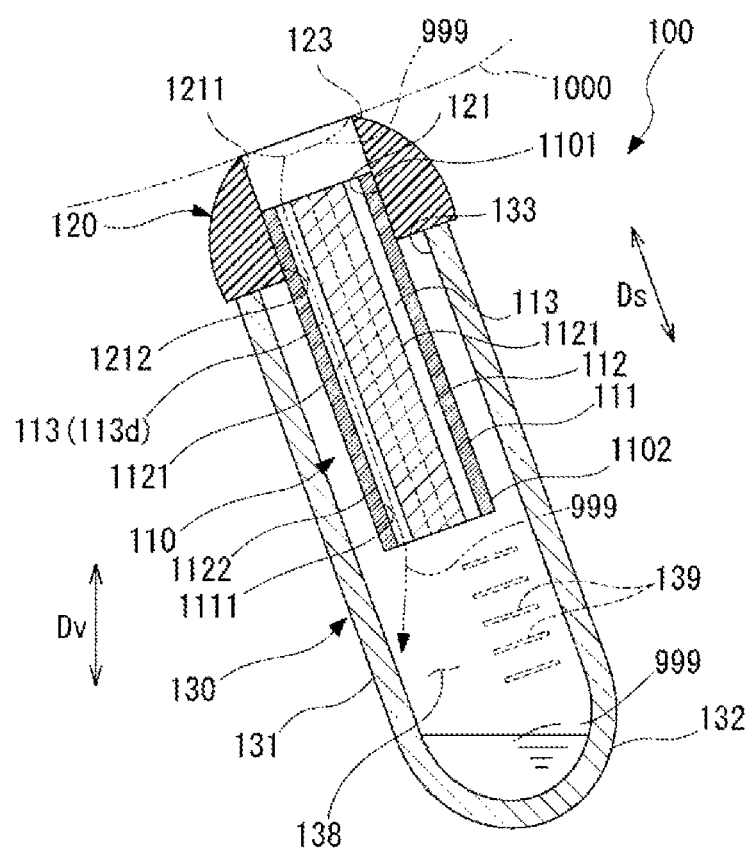
FIG. 3 illustrates the manner in which liquid is collected in the liquid collector illustrated in FIG. 1.

FIGS. 1 to 3 illustrate a liquid collector 100 according to an embodiment. As illustrated in FIGS. 1 to 3, the liquid collector 100 includes a flow passage member 110, a contact member 120, and a container 130. The liquid collector 100 collects liquid.

The flow passage member 110 includes an outside tube 111 and an inside member 112. The outside tube 111 has a tubular shape that extends in a pipe axis direction Ds connecting one end 1101 and other end 1102 of the flow passage member 110. In the embodiment of the present disclosure, the outside tube 111 has, for example, a circular shape in cross-section when viewed in the pipe axis direction Ds. The outside tube 111 may also have, for example, an elliptical shape in cross-section when viewed in the pipe axis direction Ds. The outside tube 111 may also have, for example, a polygonal shape, such as a triangular shape, a quadrangular shape, a pentagonal shape, a hexagonal shape, or an octagonal shape in cross-section when viewed in the pipe axis direction Ds.

The inside member 112 is inserted in the outside tube 111. The inside member 112 has a columnar shape that extends in the pipe axis direction Ds. The inside member 112 has a uniform cross-sectional shape in the pipe axis direction Ds.

The inside member 112 has a plurality of grooves 1121 that extend in the pipe axis direction Ds. The grooves 1121 are arranged with equal intervals therebetween in a circumferential direction around a central axis of the inside member 112. Each groove 1121 is recessed radially inward from an outer peripheral surface 1122 of the inside member 112. Each groove 1121 extends continuously in the pipe axis direction Ds.

The outer peripheral surface 1122 of the inside member 112 inserted in the outside tube 111 is in contact with, or slightly spaced from, an inner peripheral surface 1111 of the outside tube 111. In the flow passage member 110, flow passages 113 are defined between the inner peripheral surface 1111 of the outside tube 111 and the grooves 1121 in the inside member 112. The flow passages 113 extend in the pipe axis direction Ds to connect the one end 1101 and the other end 1102 of the flow passage member 110.

Thus, the flow passage member 110 includes a plurality of flow passages 113. The flow passages 113 extend in the pipe axis direction Ds connecting the one end 1101 and the other end 1102. The flow passages 113 are substantially parallel to each other.

The contact member 120 is disposed at the one end 1101 of the flow passage member 110. The contact member 120 is configured to come into contact with a target from which the liquid is to be collected. The contact member 120 may include, or may be, an elastic material. When the contact member 120 includes an elastic material, the contact member 120 may be a combination of a portion made of the elastic material and a portion made of another material.

The contact member 120 has a flow-passage-member receiving hole 121. The flow-passage-member receiving hole 121 extends in the pipe axis direction Ds. The flow-passage-member receiving hole 121 has an inlet opening 1211 at an end thereof at one side in the pipe axis direction Ds. The inlet opening 1211 opens at a side opposite to a side at which the flow passage member 110 is disposed in the pipe axis direction Ds. The inlet opening 1211 comes into contact with a surface of the target from which the liquid is to be collected and allows introduction of the liquid that is on or near the surface.

The flow-passage-member receiving hole 121 has an outlet opening 1212 at an end thereof at the other side in the pipe axis direction Ds. The outlet opening 1212 opens at the side at which the flow passage member 110 is disposed in the pipe axis direction Ds. The outlet opening 1212 is connected to the inlet opening 1211 to provide fluid communication through the flow-passage-member receiving hole 121.

The one end 1101 of the flow passage member 110 is fitted into the outlet opening 1212 of the contact member 120 from the other side in the pipe axis direction Ds. The one end 1101 of the flow passage member 110 is disposed at a position recessed from the inlet opening 1211 of the contact member 120 toward the other side in the pipe axis direction Ds. The one end 1101 of the flow passage member 110 does not project from the contact member 120 toward the one side in the pipe axis direction Ds. Thus, the outlet opening 1212 is connected to the flow passage member 110 to provide fluid communication.

The contact member 120 has a contact surface 123 in a region around the inlet opening 1211. The contact surface 123 extends over the entirety of a region of the contact member 120 excluding a region facing the container 130 at the other side in the pipe axis direction Ds. The contact surface 123 is configured to come into contact with the surface of the target from which the liquid is to be collected. The contact surface 123 projects from the one end 1101 of the flow passage member 110 toward the one side in the pipe axis direction Ds. At least a portion of the contact surface 123 is spherical.

The container 130 receives the liquid discharged from the flow passages 113 at the other end 1102 of the flow passage member 110. The container 130 includes a peripheral wall 131 and a bottom portion 132 that are integrated together.

The peripheral wall 131 has a tubular shape that extends in the pipe axis direction Ds. In the embodiment of the present disclosure, the peripheral wall 131 has a uniform diameter in the pipe axis direction Ds. The peripheral wall 131 has an inner diameter greater than an outer diameter of the flow passage member 110. Accordingly, an inner peripheral surface of the peripheral wall 131 and an outer peripheral surface of the flow passage member 110 are spaced from each other in a radial direction orthogonal to the pipe axis direction Ds.

The bottom portion 132 blocks the peripheral wall 131 at the other side in the pipe axis direction Ds. The bottom portion 132 is, for example, hemispherical. The bottom portion 132 may also be plate-shaped and extend along a plane substantially orthogonal to the pipe axis direction Ds. The container 130 is formed of the peripheral wall 131 and the bottom portion 132 so as to have a tubular shape with a bottom.

The container 130 has an opening 133 at the one side in the pipe axis direction Ds (side opposite to the side at which the bottom portion 132 is provided). The contact member 120 is disposed to close the opening 133 of the container 130.

The bottom portion 132 of the container 130 is spaced from the other end 1102 of the flow passage member 110 in the pipe axis direction Ds. Accordingly, a reservoir space 138 that stores the liquid is defined between the bottom portion 132 of the container 130 and the other end 1102 of the flow passage member 110.

At least a portion or the entirety of the container 130 may be made of a material having transparency characteristics that allow optical observation of the inside of the container 130 from the outside. Examples of the material having transparency characteristics that allow optical observation of the inside of the container 130 from the outside include, but are not limited to, resin materials and glass materials. The material having transparency characteristics that allow optical observation of the inside of the container 130 from the outside may have transparency characteristics such that the amount of the liquid accumulated in the container body is observable visually or with a camera from the outside of the container 130.

The container 130 has scale marks 139 that indicate an amount of the liquid received in the container 130.

To collect liquid in the above-described liquid collector 100, the inlet opening 1211 of the contact member 120 is brought into contact with the surface of the target from which the liquid is to be collected. In some embodiments, the liquid collector 100 collects body fluid (liquid) secreted in a target subject. Examples of a part of the target subject in which the body fluid is secreted include, but are not limited to, an eyeball, regions around the eye at the inner and outer corners of the eye, a part in the oral cavity (for example, a sublingual region), a part in the nasal cavity, and the skin surface. In the embodiment of the present disclosure, the liquid collector 100 collects tear fluid from the outer corner the target subject's eye as the liquid. In this case, as illustrated in FIG. 3, the inlet opening 1211 of the contact member 120 is brought into contact with a surface 1000 of the target subject's face at or around the outer corner of the eye. Accordingly, liquid 999 that is on or near the surface 1000 is introduced through the inlet opening 1211 by capillarity. Thus, the liquid 999 (tear fluid) on or near the surface 1000 is introduced through the inlet opening 1211.

The liquid 999 introduced through the inlet opening 1211 enters the flow passages 113 at the one end 1101 of the flow passage member 110, and flows through the flow passages 113 toward the other end 1102. The liquid 999 is discharged from the flow passages 113 at the other end 1102 of the flow passage member 110. The liquid 999 discharged from the flow passages 113 is stored in the reservoir space 138 of the container 130. Thus, the liquid can be efficiently collected.

When the pipe axis direction Ds of the liquid collector 100 is inclined with respect to a vertical direction Dv upon collection of the liquid 999, the liquid 999 introduced through the inlet opening 1211 flows downward in the vertical direction Dv. The liquid 999 introduced through the inlet opening 1211 tends to flow into a flow passage 113d, which is one of the flow passages 113 in the flow passage member 110 that is positioned in a lower region in the vertical direction Dv. When the liquid 999 flows into the reservoir space 138, an amount of air corresponding to the volume of the liquid 999 that flows into the reservoir space 138 is pushed out of the reservoir space 138. The air pushed out of the reservoir space 138 moves toward the inlet opening 1211 through, for example, one or more of the flow passages 113 that are positioned in an upper region in the vertical direction Dv and through which the liquid 999 does not flow.

Figure 4:
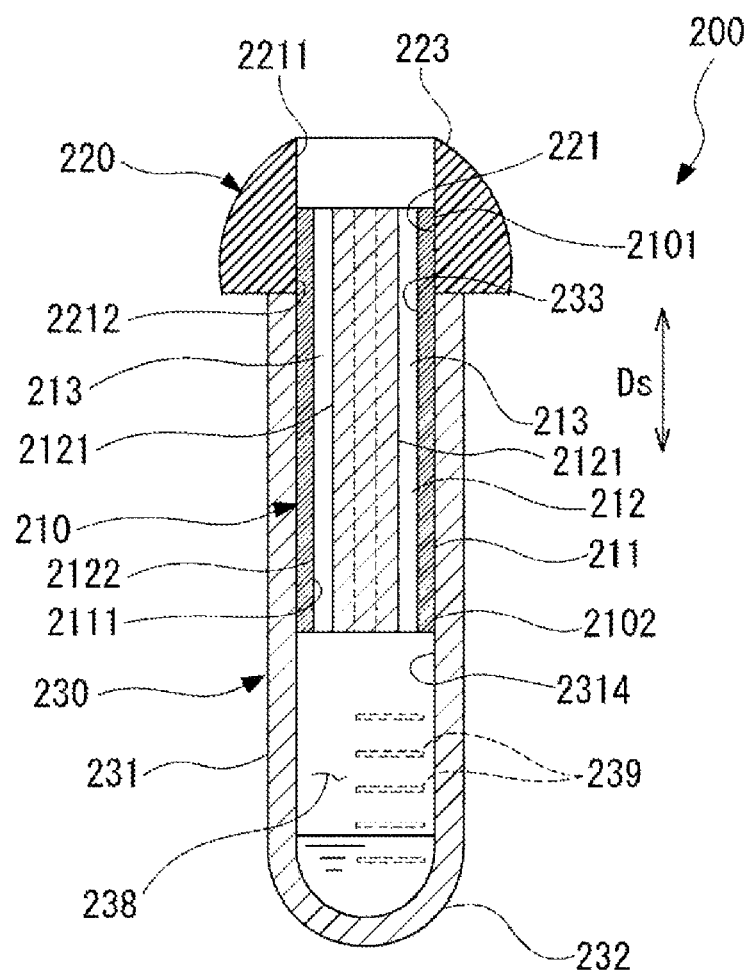
FIG. 4 is a sectional view of a liquid collector according to an embodiment.
Figure 5:
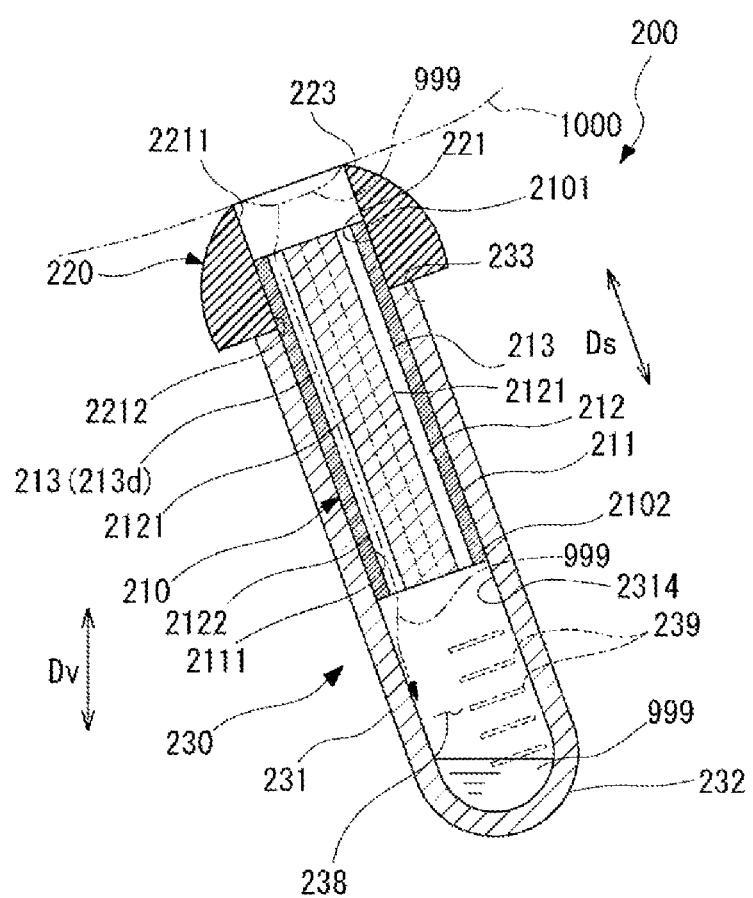
FIG. 5 illustrates the manner in which liquid is collected in the liquid collector illustrated in FIG. 4.

FIGS. 4 and 5 illustrate a liquid collector 200 according to an embodiment. As illustrated in FIGS. 4 and 5, the liquid collector 200 includes a flow passage member 210, a contact member 220, and a container 230. The liquid collector 200 collects liquid.

The flow passage member 210 includes an outside tube 211 and an inside member 212. The outside tube 211 has a tubular shape that extends in a pipe axis direction Ds connecting one end 2101 and other end 2102 of the flow passage member 210. In the embodiment of the present disclosure, the outside tube 211 has, for example, a circular shape in cross-section when viewed in the pipe axis direction Ds. The outside tube 211 may also have, for example, an elliptical shape in cross-section when viewed in the pipe axis direction Ds. The outside tube 211 may also have, for example, a polygonal shape, such as a triangular shape, a quadrangular shape, a pentagonal shape, a hexagonal shape, or an octagonal shape in cross-section when viewed in the pipe axis direction Ds.

The inside member 212 is inserted in the outside tube 211. The inside member 212 has a columnar shape that extends in the pipe axis direction Ds. The inside member 212 has a uniform cross-sectional shape in the pipe axis direction Ds. The inside member 212 has a plurality of grooves 2121 that extend in the pipe axis direction Ds. The grooves 2121 are arranged with equal intervals therebetween in a circumferential direction around a central axis of the inside member 212. Each groove 2121 is recessed radially inward from an outer peripheral surface 2122 of the inside member 212. Each groove 2121 extends continuously in the pipe axis direction Ds.

The outer peripheral surface 2122 of the inside member 212 inserted in the outside tube 211 is in contact with, or slightly spaced from, an inner peripheral surface 2111 of the outside tube 211. In the flow passage member 210, flow passages 213 are defined between the inner peripheral surface 2111 of the outside tube 211 and the grooves 2121 in the inside member 212. The flow passages 213 extend in the pipe axis direction Ds to connect the one end 2101 and the other end 2102 of the flow passage member 210.

Thus, the flow passage member 210 includes a plurality of flow passages 213. The flow passages 213 extend in the pipe axis direction Ds connecting the one end 2101 and the other end 2102. The flow passages 213 are substantially parallel to each other.

The contact member 220 is disposed at the one end 2101 of the flow passage member 210. The contact member 220 is configured to come into contact with a target from which the liquid is to be collected. The contact member 220 may include, or may be, an elastic material. When the contact member 220 includes an elastic material, the contact member 220 may be a combination of a portion made of the elastic material and a portion made of another material.

The contact member 220 has a flow-passage-member receiving hole 221. The flow-passage-member receiving hole 221 extends in the pipe axis direction Ds. The flow-passage-member receiving hole 221 has an inlet opening 2211 at an end thereof at one side in the pipe axis direction Ds. The inlet opening 2211 opens at a side opposite to a side at which the flow passage member 210 is disposed in the pipe axis direction Ds. The inlet opening 2211 comes into contact with a surface of the target from which the liquid is to be collected and allows introduction of the liquid that is on or near the surface. The flow-passage-member receiving hole 221 has an outlet opening 2212 at an end thereof at the other side in the pipe axis direction Ds. The outlet opening 2212 opens at the side at which the flow passage member 210 is disposed in the pipe axis direction Ds. The outlet opening 2212 is connected to the inlet opening 2211 to provide fluid communication through the flow-passage-member receiving hole 221.

The one end 2101 of the flow passage member 210 is fitted into the outlet opening 2212 of the contact member 220 from the other side in the pipe axis direction Ds. The one end 2101 of the flow passage member 210 is disposed at a position recessed from the inlet opening 2211 of the contact member 220 toward the other side in the pipe axis direction Ds. The one end 2101 of the flow passage member 210 does not project from the contact member 220 toward the one side in the pipe axis direction Ds. Thus, the outlet opening 2212 is connected to the flow passage member 210 to provide fluid communication.

The contact member 220 has a contact surface 223 in a region around the inlet opening 2211. The contact surface 223 is configured to come into contact with the surface of the target from which the liquid is to be collected. The contact surface 223 projects from the one end 2101 of the flow passage member 210 toward the one side in the pipe axis direction Ds. At least a portion of the contact surface 223 is spherical. The contact surface 223 is spherical over the entirety of a region of the contact member 220 excluding a region facing the container 230 at the other side in the pipe axis direction Ds.

The container 230 receives the liquid discharged from the flow passages 213 at the other end 2102 of the flow passage member 210. The container 230 includes a peripheral wall 231 and a bottom portion 232 that are integrated together.

The peripheral wall 231 has a tubular shape that extends in the pipe axis direction Ds. In the embodiment of the present disclosure, the peripheral wall 231 has a uniform diameter in the pipe axis direction Ds. The peripheral wall 231 has an inner diameter substantially equal to an outer diameter of the flow passage member 210. Accordingly, the other end 2102 of the flow passage member 210 is in contact with an inner peripheral surface 2314 of the peripheral wall 231. When the other end 2102 of the flow passage member 210 is in contact with the inner peripheral surface 2314 of the peripheral wall 231 as described above, the liquid in the flow passages 213 of the flow passage member 210 easily moves along the inner peripheral surface 2314 of the peripheral wall 231.

The bottom portion 232 blocks the peripheral wall 231 at the other side in the pipe axis direction Ds. The bottom portion 232 is, for example, hemispherical. The bottom portion 232 may also be plate-shaped and extend along a plane substantially orthogonal to the pipe axis direction Ds. The container 230 is formed of the peripheral wall 231 and the bottom portion 232 so as to have a tubular shape with a bottom.

The container 230 has an opening 233 at the one side in the pipe axis direction Ds (side opposite to the side at which the bottom portion 232 is provided). The contact member 220 is disposed to close the opening 233 of the container 230.

The bottom portion 232 of the container 230 is spaced from the other end 2102 of the flow passage member 210 in the pipe axis direction Ds. Accordingly, a reservoir space 238 that stores the liquid is defined between the bottom portion 232 of the container 230 and the other end 2102 of the flow passage member 210.

At least a portion or the entirety of the container 230 may be made of a material having transparency characteristics that allow optical observation of the inside of the container 230 from the outside. Examples of the material having transparency characteristics that allow optical observation of the inside of the container 230 from the outside include, but are not limited to, resin materials and glass materials. The material having transparency characteristics that allow optical observation of the inside of the container 230 from the outside may have transparency characteristics such that the amount of the liquid accumulated in the container body is observable visually or with a camera from the outside of the container 230.

The container 230 has scale marks 239 that indicate an amount of the liquid received in the container 230.

To collect liquid in the above-described liquid collector 200, the inlet opening 2211 of the contact member 220 is brought into contact with a surface 1000 of the target from which the liquid is to be collected, as illustrated in FIG. 5. Accordingly, liquid 999 that is on or near the surface 1000 is introduced through the inlet opening 2211 by capillarity. The liquid 999 introduced through the inlet opening 2211 enters the flow passages 213 at the one end 2101 of the flow passage member 210. The liquid 999 flows toward the other end 2102 through the flow passages 213. The liquid 999 is discharged from the flow passages 213 at the other end 2102 of the flow passage member 210. Since the outer peripheral surface 2122 of the flow passage member 210 is in contact with the inner peripheral surface 2314 of the container 230, the liquid 999 discharged from the flow passages 213 easily flows along the inner peripheral surface 2314 of the container 230. The liquid 999 flows downward along the inner peripheral surface 2314, and is stored in the reservoir space 238 of the container 230. Thus, the liquid can be efficiently collected.

When the pipe axis direction Ds of the liquid collector 200 is inclined with respect to a vertical direction Dv upon collection of the liquid 999, the liquid 999 introduced through the inlet opening 2211 flows downward in the vertical direction Dv. The liquid 999 introduced through the inlet opening 2211 tends to flow into a flow passage 213*d*, which is one of the flow passages 213 in the flow passage member 210 that is positioned in a lower region in the vertical direction Dv.

When the liquid 999 flows into the reservoir space 238, an amount of air corresponding to the volume of the liquid 999 that flows into the reservoir space 238 is pushed out of the reservoir space 238. The air pushed out of the reservoir space 238 flows through one or more of the flow passages 213 that are positioned in an upper region in the vertical direction Dv and through which the liquid 999 does not flow, and is discharged to the outside from the inlet opening 2211.

Figure 6:
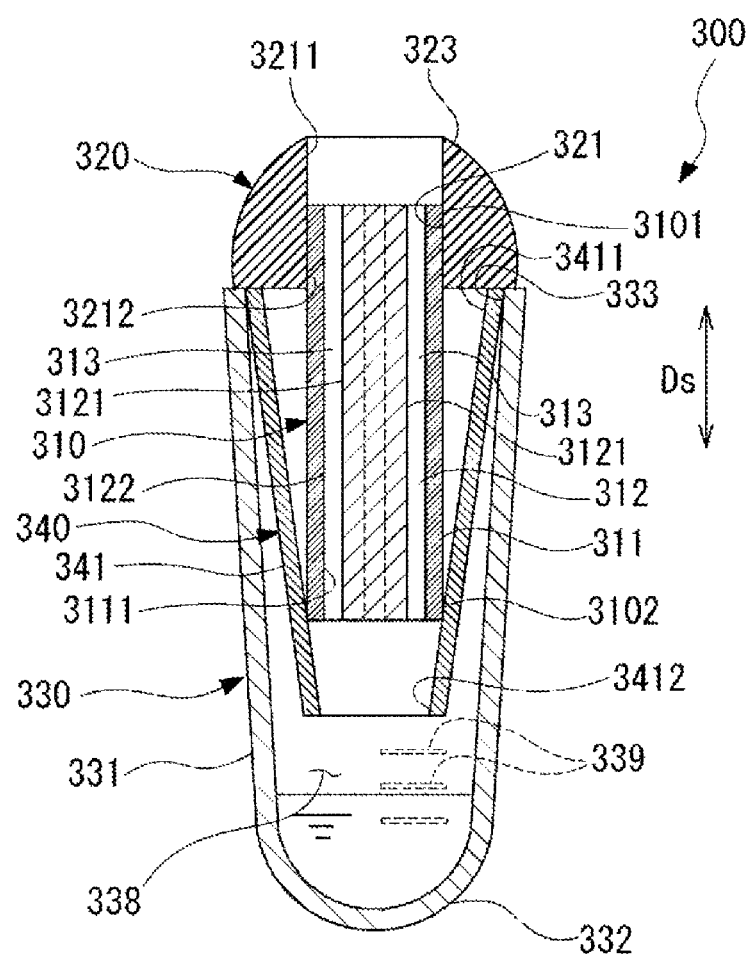
FIG. 6 is a sectional view of a liquid collector according to an embodiment.
Figure 7:
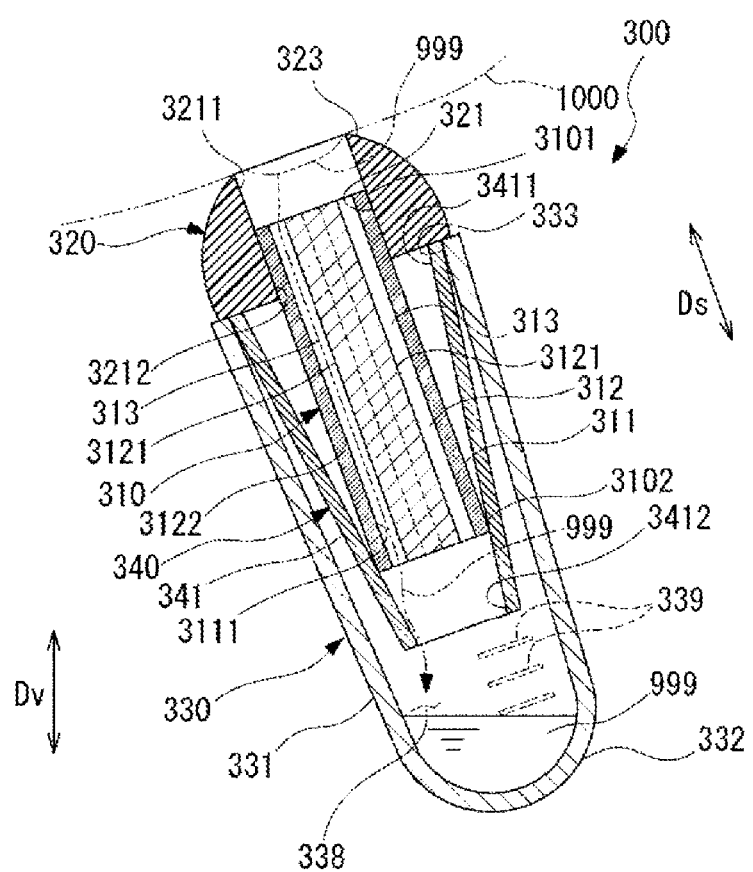
FIG. 7 illustrates the manner in which liquid is collected in the liquid collector illustrated in FIG. 6.

FIGS. 6 and 7 illustrate a liquid collector 300 according to an embodiment. As illustrated in FIGS. 6 and 7, the liquid collector 300 includes a flow passage member 310, a contact member 320, a container 330, and an inner member 340. The liquid collector 300 collects liquid.

The flow passage member 310 includes an outside tube 311 and an inside member 312.

The outside tube 311 has a tubular shape that extends in a pipe axis direction Ds connecting one end 3101 and other end 3102 of the flow passage member 310. In the embodiment of the present disclosure, the outside tube 311 has, for example, a circular shape in cross-section when viewed in the pipe axis direction Ds. The outside tube 311 may also have, for example, an elliptical shape in cross-section when viewed in the pipe axis direction Ds. The outside tube 311 may also have, for example, a polygonal shape, such as a triangular shape, a quadrangular shape, a pentagonal shape, a hexagonal shape, or an octagonal shape in cross-section when viewed in the pipe axis direction Ds.

The inside member 312 is inserted in the outside tube 311. The inside member 312 has a columnar shape that extends in the pipe axis direction Ds. The inside member 312 has a uniform cross-sectional shape in the pipe axis direction Ds. The inside member 312 has a plurality of grooves 3121 that extend in the pipe axis direction Ds. The grooves 3121 are arranged with equal intervals therebetween in a circumferential direction around a central axis of the inside member 312. Each groove 3121 is recessed radially inward from an outer peripheral surface 3122 of the inside member 312. Each groove 3121 extends continuously in the pipe axis direction Ds.

The outer peripheral surface 3122 of the inside member 312 inserted in the outside tube 311 is in contact with, or slightly spaced from, an inner peripheral surface 3111 of the outside tube 311. In the flow passage member 310, flow passages 313 are defined between the inner peripheral surface 3111 of the outside tube 311 and the grooves 3121 in the inside member 312. The flow passages 313 extend in the pipe axis direction Ds to connect the one end 3101 and the other end 3102 of the flow passage member 310.

Thus, the flow passage member 310 includes a plurality of flow passages 313. The flow passages 313 extend in the pipe axis direction Ds connecting the one end 3101 and the other end 3102. The flow passages 313 are substantially parallel to each other.

The contact member 320 is disposed at the one end 3101 of the flow passage member 310. The contact member 320 is configured to come into contact with a target from which the liquid is to be collected. The contact member 320 may include, or may be, an elastic material. When the contact member 320 includes an elastic material, the contact member 320 may be a combination of a portion made of the elastic material and a portion made of another material.

The contact member 320 has a flow-passage-member receiving hole 321. The flow-passage-member receiving hole 321 extends in the pipe axis direction Ds. The flow-passage-member receiving hole 321 has an inlet opening 3211 at an end thereof at one side in the pipe axis direction Ds. The inlet opening 3211 opens at a side opposite to a side at which the flow passage member 310 is disposed in the pipe axis direction Ds. The inlet opening 3211 comes into contact with a surface of the target from which the liquid is to be collected and allows introduction of the liquid that is on or near the surface.

The flow-passage-member receiving hole 321 has an outlet opening 3212 at an end thereof at the other side in the pipe axis direction Ds. The outlet opening 3212 opens at the side at which the flow passage member 310 is disposed in the pipe axis direction Ds. The outlet opening 3212 is connected to the inlet opening 3211 to provide fluid communication through the flow-passage-member receiving hole 321.

The one end 3101 of the flow passage member 310 is fitted into the outlet opening 3212 of the contact member 320 from the other side in the pipe axis direction Ds. The one end 3101 of the flow passage member 310 is disposed at a position recessed from the inlet opening 3211 of the contact member 320 toward the other side in the pipe axis direction Ds. The one end 3101 of the flow passage member 310 does not project from the contact member 320 toward the one side in the pipe axis direction Ds. Thus, the outlet opening 3212 is connected to the flow passage member 310 to provide fluid communication.

The contact member 320 has a contact surface 323 in a region around the inlet opening 3211. The contact surface 323 is configured to come into contact with the surface of the target from which the liquid is to be collected. The contact surface 323 projects from the one end 3101 of the flow passage member 310 toward the one side in the pipe axis direction Ds. At least a portion of the contact surface 323 is spherical. The contact surface 323 is spherical over the entirety of a region of the contact member 320 excluding a region facing the container 330 at the other side in the pipe axis direction Ds.

The container 330 receives the liquid discharged from the flow passages 313 at the other end 3102 of the flow passage member 310. The container 330 includes a peripheral wall 331 and a bottom portion 332 that are integrated together.

The peripheral wall 331 has a tubular shape that extends in the pipe axis direction Ds. In the embodiment of the present disclosure, the peripheral wall 331 has an inner diameter that gradually decreases toward the bottom portion 332 at the other side from the one side in the pipe axis direction Ds.

The bottom portion 332 blocks the peripheral wall 331 at the other side in the pipe axis direction Ds. The bottom portion 332 is, for example, hemispherical. The bottom portion 332 may also be plate-shaped and extend along a plane substantially orthogonal to the pipe axis direction Ds. The container 330 is formed of the peripheral wall 331 and the bottom portion 332 so as to have a tubular shape with a bottom.

The container 330 has an opening 333 at the one side in the pipe axis direction Ds (side opposite to the side at which the bottom portion 332 is provided). The contact member 320 is disposed to close the opening 333 of the container 330.

The bottom portion 332 of the container 330 is spaced from the other end 3102 of the flow passage member 310 in the pipe axis direction Ds. Accordingly, a reservoir space 338 that stores the liquid is defined between the bottom portion 332 of the container 330 and the other end 3102 of the flow passage member 310.

At least a portion or the entirety of the container 330 may be made of a material having transparency characteristics that allow optical observation of the inside of the container 330 from the outside. Examples of the material having transparency characteristics that allow optical observation of the inside of the container 330 from the outside include, but are not limited to, resin materials and glass materials. The material having transparency characteristics that allow optical observation of the inside of the container 330 from the outside may have transparency characteristics such that the amount of the liquid accumulated in the container body is observable visually or with a camera from the outside of the container 330.

The container 330 has scale marks 339 that indicate an amount of the liquid received in the container 330.

The inner member 340 is disposed in the container 330. The inner member 340 includes a cone-shaped portion 341 having an inner diameter that gradually decreases toward the bottom portion 332 in the pipe axis direction Ds. In the embodiment of the present disclosure, the cone-shaped portion 341 is formed over the entire region of the inner member 340 in the pipe axis direction Ds. In some embodiments, the cone-shaped portion 341 may be formed over only a partial region of the inner member 340 in the pipe axis direction Ds. The cone-shaped portion 341 has a first opening 3411 at an end adjacent to the opening 333, and an inner diameter of the first opening 3411 is greater than an outer diameter of the flow passage member 310 at the other end 3102. The cone-shaped portion 341 has a second opening 3412 at an end adjacent to the bottom portion 332, and an inner diameter of the second opening 3412 is less than the outer diameter of the flow passage member 310 at the other end 3102. Accordingly, the other end 3102 of the flow passage member 310 is in contact with an inner peripheral surface of the cone-shaped portion 341 at a position between the first opening 3411 and the second opening 3412 of the cone-shaped portion 341. When the other end 3102 of the flow passage member 310 is in contact with the cone-shaped portion 341 as described above, the liquid in the flow passages 313 of the flow passage member 310 easily flows along the inner peripheral surface of the cone-shaped portion 341.

To collect liquid in the above-described liquid collector 300, the inlet opening 3211 of the contact member 320 is brought into contact with a surface 1000 of the target from which the liquid is to be collected, as illustrated in FIG. 7. Accordingly, liquid 999 that is on or near the surface 1000 is introduced through the inlet opening 3211 by capillarity. The liquid 999 introduced through the inlet opening 3211 enters the flow passages 313 at the one end 3101 of the flow passage member 310. The liquid 999 flows toward the other end 3102 through the flow passages 313. The liquid 999 is discharged from the flow passages 313 at the other end 3102 of the flow passage member 310. The liquid 999 discharged from the flow passages 313 flows downward along the inner peripheral surface of the cone-shaped portion 341. The liquid 999 falls from the second opening 3412 of the cone-shaped portion 341, and is stored in the reservoir space 338 of the container 330. Thus, the liquid can be efficiently collected.

Figure 8:
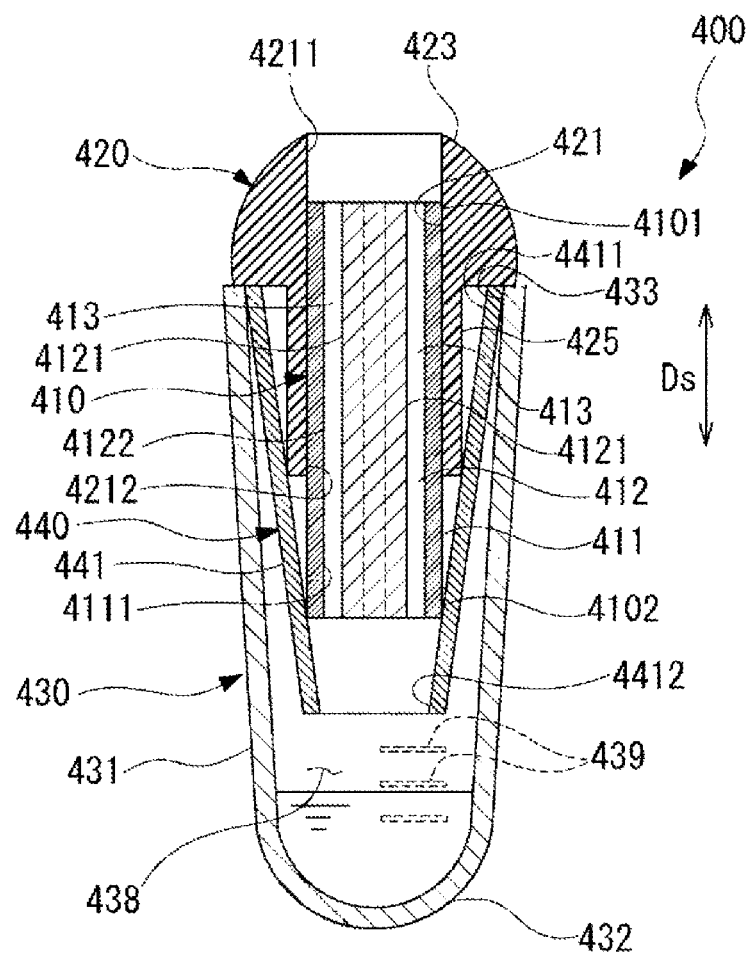
FIG. 8 is a sectional view of a liquid collector according to an embodiment.
Figure 9:
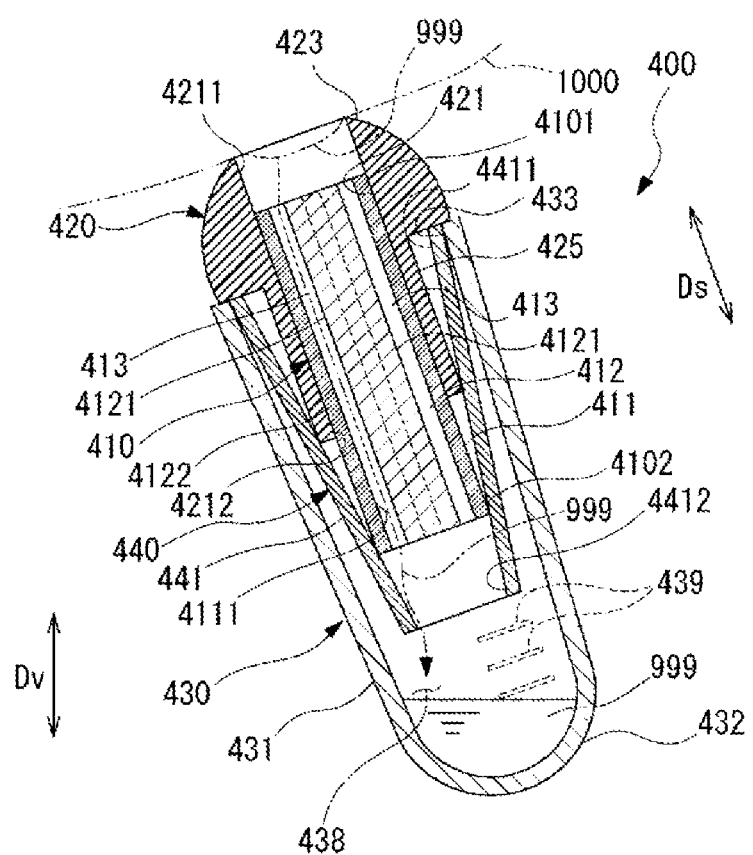
FIG. 9 illustrates the manner in which liquid is collected in the liquid collector illustrated in FIG. 8.

FIGS. 8 and 9 illustrate a liquid collector 400 according to an embodiment. As illustrated in FIGS. 8 and 9, the liquid collector 400 includes a flow passage member 410, a contact member 420, a container 430, and an inner member 440. The liquid collector 400 collects liquid.

The flow passage member 410 includes an outside tube 411 and an inside member 412.

The outside tube 411 has a tubular shape that extends in a pipe axis direction Ds connecting one end 4101 and other end 4102 of the flow passage member 410. In the embodiment of the present disclosure, the outside tube 411 has, for example, a circular shape in cross-section when viewed in the pipe axis direction Ds. The outside tube 411 may also have, for example, an elliptical shape in cross-section when viewed in the pipe axis direction Ds. The outside tube 411 may also have, for example, a polygonal shape, such as a triangular shape, a quadrangular shape, a pentagonal shape, a hexagonal shape, or an octagonal shape in cross-section when viewed in the pipe axis direction Ds.

The inside member 412 is inserted in the outside tube 411. The inside member 412 has a columnar shape that extends in the pipe axis direction Ds. The inside member 412 has a uniform cross-sectional shape in the pipe axis direction Ds. The inside member 412 has a plurality of grooves 4121 that extend in the pipe axis direction Ds. The grooves 4121 are arranged with equal intervals therebetween in a circumferential direction around a central axis of the inside member 412. Each groove 4121 is recessed radially inward from an outer peripheral surface 4122 of the inside member 412. Each groove 4121 extends continuously in the pipe axis direction Ds.

The outer peripheral surface 4122 of the inside member 412 inserted in the outside tube 411 is in contact with, or slightly spaced from, an inner peripheral surface 4111 of the outside tube 411. In the flow passage member 410, flow passages 413 are defined between the inner peripheral surface 4111 of the outside tube 411 and the grooves 4121 in the inside member 412. The flow passages 413 extend in the pipe axis direction Ds to connect the one end 4101 and the other end 4102 of the flow passage member 410.

Thus, the flow passage member 410 includes a plurality of flow passages 413. The flow passages 413 extend in the pipe axis direction Ds connecting the one end 4101 and the other end 4102. The flow passages 413 are substantially parallel to each other.

The contact member 420 is disposed at the one end 4101 of the flow passage member 410. The contact member 420 is configured to come into contact with a target from which the liquid is to be collected. The contact member 420 may include, or may be, an elastic material. When the contact member 420 includes an elastic material, the contact member 420 may be a combination of a portion made of the elastic material and a portion made of another material.

The contact member 420 has a flow-passage-member receiving hole 421. The flow-passage-member receiving hole 421 extends in the pipe axis direction Ds. The flow-passage-member receiving hole 421 has an inlet opening 4211 at an end thereof at one side in the pipe axis direction Ds. The inlet opening 4211 opens at a side opposite to a side at which the flow passage member 410 is disposed in the pipe axis direction Ds. The inlet opening 4211 comes into contact with a surface of the target from which the liquid is to be collected and allows introduction of the liquid that is on or near the surface.

The contact member 420 includes a sleeve 425 that is integral therewith. The sleeve 425 projects from the contact member 420 toward the other end 4102 of the flow passage member 410. The sleeve 425 extends in the pipe axis direction Ds. The sleeve 425 is inserted in the container 430.

The flow-passage-member receiving hole 421 has an outlet opening 4212 at an end thereof at the other side in the pipe axis direction Ds. In the embodiment of the present disclosure, the outlet opening 4212 is formed in the sleeve 425. The outlet opening 4212 opens at the side at which the flow passage member 410 is disposed in the pipe axis direction Ds. The outlet opening 4212 is connected to the inlet opening 4211 to provide fluid communication through the flow-passage-member receiving hole 421.

The one end 4101 of the flow passage member 410 is fitted into the outlet opening 4212 of the contact member 420 from the other side in the pipe axis direction Ds. Since the contact member 420 includes the sleeve 425, the one end 4101 of the flow passage member 410 is retained by the contact member 420 (including the sleeve 425) over a longer length in the pipe axis direction Ds. Accordingly, the flow passage member 410 is more strongly supported. Thus, the outlet opening 4212 is connected to the flow passage member 410 to provide fluid communication.

The one end 4101 of the flow passage member 410 is disposed at a position recessed from the inlet opening 4211 of the contact member 420 toward the other side in the pipe axis direction Ds. The one end 4101 of the flow passage member 410 does not project from the contact member 420 toward the one side in the pipe axis direction Ds.

The contact member 420 has a contact surface 423 in a region around the inlet opening 4211. The contact surface 423 is configured to come into contact with the surface of the target from which the liquid is to be collected. The contact surface 423 projects from the one end 4101 of the flow passage member 410 toward the one side in the pipe axis direction Ds. At least a portion of the contact surface 423 is spherical. The contact surface 423 is spherical over the entirety of a region of the contact member 420 excluding a region facing the container 430 at the other side in the pipe axis direction Ds.

The container 430 receives the liquid discharged from the flow passages 413 at the other end 4102 of the flow passage member 410. The container 430 includes a peripheral wall 431 and a bottom portion 432 that are integrated together.

The peripheral wall 431 has a tubular shape that extends in the pipe axis direction Ds. In the embodiment of the present disclosure, the peripheral wall 431 has an inner diameter that gradually decreases toward the bottom portion 432 at the other side from the one side in the pipe axis direction Ds.

The bottom portion 432 blocks the peripheral wall 431 at the other side in the pipe axis direction Ds. The bottom portion 432 is, for example, hemispherical. The bottom portion 432 may also be plate-shaped and extend along a plane substantially orthogonal to the pipe axis direction Ds. The container 430 is formed of the peripheral wall 431 and the bottom portion 432 so as to have a tubular shape with a bottom.

The container 430 has an opening 433 at the one side in the pipe axis direction Ds (side opposite to the side at which the bottom portion 432 is provided). The contact member 420 is disposed to close the opening 433 of the container 430.

The bottom portion 432 of the container 430 is spaced from the other end 4102 of the flow passage member 410 in the pipe axis direction Ds. Accordingly, a reservoir space 438 that stores the liquid is defined between the bottom portion 432 of the container 430 and the other end 4102 of the flow passage member 410.

At least a portion or the entirety of the container 430 may be made of a material having transparency characteristics that allow optical observation of the inside of the container 430 from the outside. Examples of the material having transparency characteristics that allow optical observation of the inside of the container 430 from the outside include, but are not limited to, resin materials and glass materials. The material having transparency characteristics that allow optical observation of the inside of the container 430 from the outside may have transparency characteristics such that the amount of the liquid accumulated in the container body is observable visually or with a camera from the outside of the container 430.

The container 430 has scale marks 439 that indicate an amount of the liquid received in the container 430.

The inner member 440 is disposed in the container 430. The inner member 440 includes a cone-shaped portion 441 having an inner diameter that gradually decreases toward the bottom portion 432 in the pipe axis direction Ds. In the embodiment of the present disclosure, the cone-shaped portion 441 is formed over the entire region of the inner member 440 in the pipe axis direction Ds. In some embodiments, the cone-shaped portion 441 may be formed over only a partial region of the inner member 440 in the pipe axis direction Ds. The cone-shaped portion 441 has a first opening 4411 at an end adjacent to the opening 433, and an inner diameter of the first opening 4411 is greater than an outer diameter of the flow passage member 410 at the other end 4102. The cone-shaped portion 441 has a second opening 4412 at an end adjacent to the bottom portion 432, and an inner diameter of the second opening 4412 is less than the outer diameter of the flow passage member 410 at the other end 4102. Accordingly, the other end 4102 of the flow passage member 410 is in contact with an inner peripheral surface of the cone-shaped portion 441 at a position between the first opening 4411 and the second opening 4412 of the cone-shaped portion 441. When the other end 4102 of the flow passage member 410 is in contact with the cone-shaped portion 441 as described above, the liquid in the flow passages 413 of the flow passage member 410 easily flows along the cone-shaped portion 441.

To collect liquid in the above-described liquid collector 400, the inlet opening 4211 of the contact member 420 is brought into contact with a surface 1000 of the target from which the liquid is to be collected, as illustrated in FIG. 9. Accordingly, liquid 999 that is on or near the surface 1000 is introduced through the inlet opening 4211 by capillarity. The liquid 999 introduced through the inlet opening 4211 enters the flow passages 413 at the one end 4101 of the flow passage member 410. The liquid 999 flows toward the other end 4102 through the flow passages 413. The liquid 999 is discharged from the flow passages 413 at the other end 4102 of the flow passage member 410. The liquid 999 discharged from the flow passages 413 flows downward along the inner peripheral surface of the cone-shaped portion 441. The liquid 999 falls from the second opening 4412 of the cone-shaped portion 441, and is stored in the reservoir space 438 of the container 430. Thus, the liquid can be efficiently collected.

Figure 10:
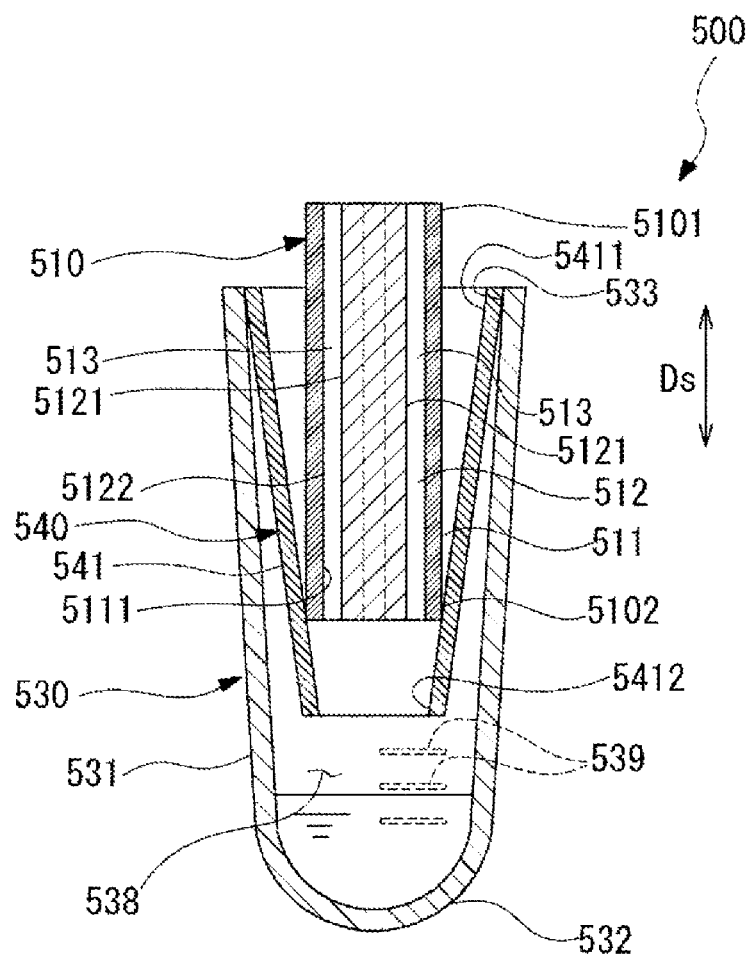
FIG. 10 is a sectional view of a liquid collector according to an embodiment.
Figure 11:
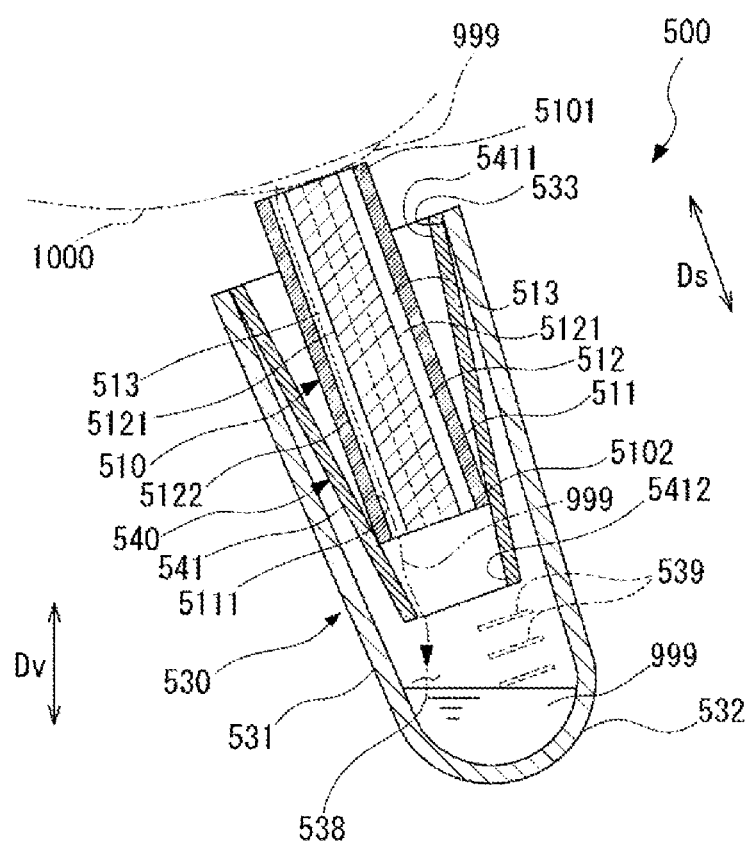
FIG. 11 illustrates the manner in which liquid is collected in the liquid collector illustrated in FIG. 10.

FIGS. 10 and 11 illustrate a liquid collector 500 according to an embodiment. As illustrated in FIGS. 10 and 11, the liquid collector 500 includes a flow passage member 510, a container 530, and an inner member 540. The liquid collector 500 collects liquid.

The flow passage member 510 includes an outside tube 511 and an inside member 512.

The outside tube 511 has a tubular shape that extends in a pipe axis direction Ds connecting one end 5101 and other end 5102 of the flow passage member 510. In the embodiment of the present disclosure, the outside tube 511 has, for example, a circular shape in cross-section when viewed in the pipe axis direction Ds. The outside tube 511 may also have, for example, an elliptical shape in cross-section when viewed in the pipe axis direction Ds. The outside tube 511 may also have, for example, a polygonal shape, such as a triangular shape, a quadrangular shape, a pentagonal shape, a hexagonal shape, or an octagonal shape in cross-section when viewed in the pipe axis direction Ds.

The inside member 512 is inserted in the outside tube 511. The inside member 512 has a columnar shape that extends in the pipe axis direction Ds. The inside member 512 has a uniform cross-sectional shape in the pipe axis direction Ds. The inside member 512 has a plurality of grooves 5121 that extend in the pipe axis direction Ds. The grooves 5121 are arranged with equal intervals therebetween in a circumferential direction around a central axis of the inside member 512. Each groove 5121 is recessed radially inward from an outer peripheral surface 5122 of the inside member 512. Each groove 5121 extends continuously in the pipe axis direction Ds.

The outer peripheral surface 5122 of the inside member 512 inserted in the outside tube 511 is in contact with, or slightly spaced from, an inner peripheral surface 5111 of the outside tube 511. In the flow passage member 510, flow passages 513 are defined between the inner peripheral surface 5111 of the outside tube 511 and the grooves 5121 in the inside member 512. The flow passages 513 extend in the pipe axis direction Ds to connect the one end 5101 and the other end 5102 of the flow passage member 510.

Thus, the flow passage member 510 includes a plurality of flow passages 513. The flow passages 513 extend in the pipe axis direction Ds connecting the one end 5101 and the other end 5102. The flow passages 513 are substantially parallel to each other.

The container 530 receives the liquid discharged from the flow passages 513 at the other end 5102 of the flow passage member 510. The container 530 includes a peripheral wall 531 and a bottom portion 532 that are integrated together.

The peripheral wall 531 has a tubular shape that extends in the pipe axis direction Ds. In the embodiment of the present disclosure, the peripheral wall 531 has an inner diameter that gradually decreases toward the bottom portion 532 at the other side from the one side in the pipe axis direction Ds.

The bottom portion 532 blocks the peripheral wall 531 at the other side in the pipe axis direction Ds. The bottom portion 532 is, for example, hemispherical. The bottom portion 532 may also be plate-shaped and extend along a plane substantially orthogonal to the pipe axis direction Ds. The container 530 is formed of the peripheral wall 531 and the bottom portion 532 so as to have a tubular shape with a bottom.

The container 530 has an opening 533 at one side in the pipe axis direction Ds (side opposite to the side at which the bottom portion 532 is provided). The flow passage member 510 is inserted into the container 530 through the opening 533. The bottom portion 532 of the container 530 is spaced from the other end 5102 of the flow passage member 510 in the pipe axis direction Ds. Accordingly, a reservoir space 538 that stores the liquid is defined between the bottom portion 532 of the container 530 and the other end 5102 of the flow passage member 510.

At least a portion or the entirety of the container 530 may be made of a material having transparency characteristics that allow optical observation of the inside of the container 530 from the outside. Examples of the material having transparency characteristics that allow optical observation of the inside of the container 530 from the outside include, but are not limited to, resin materials and glass materials. The material having transparency characteristics that allow optical observation of the inside of the container 530 from the outside may have transparency characteristics such that the amount of the liquid accumulated in the container body is observable visually or with a camera from the outside of the container 530.

The container 530 has scale marks 539 that indicate an amount of the liquid received in the container 530.

The inner member 540 is disposed in the container 530. The inner member 540 includes a cone-shaped portion 541 having an inner diameter that gradually decreases toward the bottom portion 532 in the pipe axis direction Ds. In the embodiment of the present disclosure, the cone-shaped portion 541 is formed over the entire region of the inner member 540 in the pipe axis direction Ds. In some embodiments, the cone-shaped portion 541 may be formed over only a partial region of the inner member 540 in the pipe axis direction Ds. The cone-shaped portion 541 has a first opening 5411 at an end adjacent to the opening 533, and an inner diameter of the first opening 5411 is greater than an outer diameter of the flow passage member 510 at the other end 5102. The cone-shaped portion 541 has a second opening 5412 at an end adjacent to the bottom portion 532, and an inner diameter of the second opening 5412 is less than the outer diameter of the flow passage member 510 at the other end 5102. Accordingly, the other end 5102 of the flow passage member 510 is in contact with an inner peripheral surface of the cone-shaped portion 541 at a position between the first opening 5411 and the second opening 5412 of the cone-shaped portion 541. When the other end 5102 of the flow passage member 510 is in contact with the cone-shaped portion 541 as described above, the liquid in the flow passages 513 of the flow passage member 510 easily flows along the cone-shaped portion 541.

To collect liquid in the above-described liquid collector 500, the one end 5101 of the flow passage member 510 is brought into contact with a surface 1000 of the target from which the liquid is to be collected, as illustrated in FIG. 11. The one end 5101 may have a hydrophilic or embossed surface. Accordingly, liquid 999 that is on or near the surface 1000 is introduced from the one end 5101 of the flow passage member 510 by capillarity. The liquid 999 introduced into the flow passage member 510 flows toward the other end 5102 through the flow passages 513. The liquid 999 is discharged from the flow passages 513 at the other end 5102 of the flow passage member 510. The liquid 999 discharged from the flow passages 513 flows downward along the inner peripheral surface of the cone-shaped portion 541. The liquid 999 falls from the second opening 5412 of the cone-shaped portion 541, and is stored in the reservoir space 538 of the container 530. Thus, the liquid can be efficiently collected.

Figure 12:
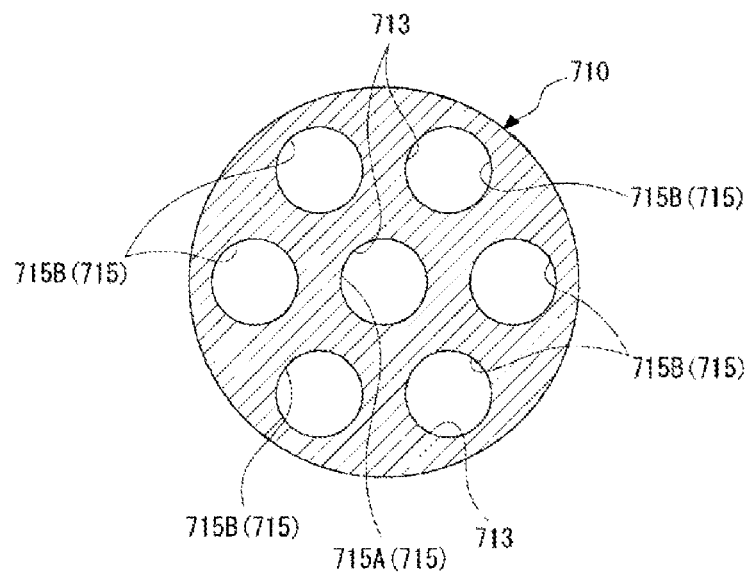
FIG. 12 is a sectional view of a flow passage member of a liquid collector according to an embodiment.

FIG. 12 illustrates a flow passage member 710 of a liquid collector according to an embodiment. Referring to FIG. 12, the flow passage member 710 has a columnar shape that extends in a pipe axis direction Ds connecting one end and other end of the flow passage member 710 (direction orthogonal to the plane of FIG. 12). In the embodiment of the present disclosure, the flow passage member 710 has, for example, a circular shape in cross-section when viewed in the pipe axis direction Ds. The flow passage member 710 may also have, for example, an elliptical shape in cross-section when viewed in the pipe axis direction Ds. The flow passage member 710 may also have, for example, a polygonal shape, such as a triangular shape, a quadrangular shape, a pentagonal shape, a hexagonal shape, or an octagonal shape in cross-section when viewed in the pipe axis direction Ds.

The flow passage member 710 has a plurality of through holes 715 that extend therethrough in the pipe axis direction Ds to connect one end and the other end of the flow passage member 710. In the embodiment of the present disclosure, a through hole 715A, which is one of the through holes 715, is disposed at the center of the flow passage member 710. Through holes 715B, which are the remaining ones of the through holes 715, are arranged in an outer peripheral region of the flow passage member 710 with equal intervals therebetween in the circumferential direction. The through holes 715 are substantially parallel to the pipe axis direction Ds.

Each through hole 715 serves as a flow passage 713 for the liquid in the flow passage member 710. The flow passage member 710 includes a plurality of flow passages 713 (through holes 715). The flow passages 713 extend in the pipe axis direction Ds connecting the one end and the other end. The flow passages 713 are substantially parallel to each other.

In some embodiments, the above-described flow passage member 710 may be used instead of the flow passage members 110, 210, 310, 410, and 510.

Figure 13:
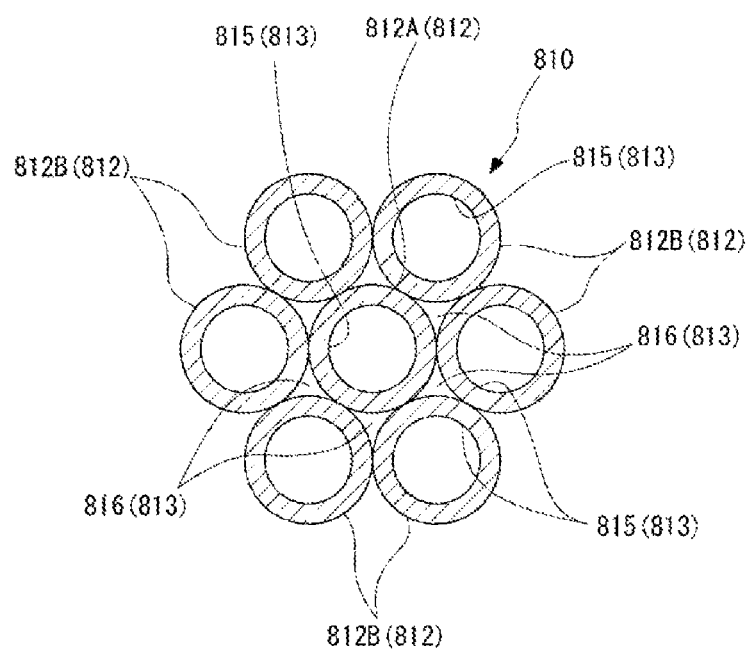
FIG. 13 is a sectional view of a flow passage member of a liquid collector according to an embodiment.

FIG. 13 illustrates a flow passage member 810 of a liquid collector according to an embodiment. As illustrated in FIG. 13, the flow passage member 810 includes a plurality of single pipes 812.

Each single pipe 812 has a tubular shape that extends in a pipe axis direction Ds (direction orthogonal to the plane of FIG. 13). Each single pipe 812 has a uniform cross-sectional shape in the pipe axis direction Ds. In the embodiment of the present disclosure, each single pipe 812 has, for example, a circular shape in cross-section when viewed in the pipe axis direction Ds. The flow passage member 810 is formed by bundling the single pipes 812. The single pipes 812 may be bundled and joined together by, for example, without limitation, adhesion, fusion bonding, or welding. The single pipes 812 may be bundled together by using, for example, without limitation, a belt-shaped band or a ring. In some embodiments, each single pipe may have a cross-sectional shape that varies in the pipe axis direction. For example, each single pipe may be a combination of two single pipes having different sizes (for example, hole diameters).

A single pipe 812A, which is one of the single pipes 812, is disposed at the center of the flow passage member 810. Single pipes 812B, which are the remaining ones of the single pipes 812, are arranged in contact with each other in the circumferential direction in a region radially outside the single pipe 812A. Each single pipe 812 extends continuously in the pipe axis direction Ds. Each single pipe 812 has a hole 815 that extends therethrough in the pipe axis direction Ds.

A plurality of gaps 816 are formed between the single pipe 812A and the single pipes 812B arranged radially outside the single pipe 812A. Each gap 816 extends continuously in the pipe axis direction Ds to connect one end and the other end of the flow passage member 810.

Thus, the holes 815 and the gaps 816 are defined in the flow passage member 810. The holes 815 and the gaps 816 each serve as a flow passage 813 for the liquid in the flow passage member 810. The flow passage member 810 has a plurality of flow passages 813 (holes 815 and gaps 816). The flow passages 813 extend in the pipe axis direction Ds connecting the one end and the other end of the flow passage member 810. The flow passages 813 are substantially parallel to each other.

In some embodiments, the above-described flow passage member 810 may be used instead of the flow passage members 110, 210, 310, 410, and 510.

Figure 14:
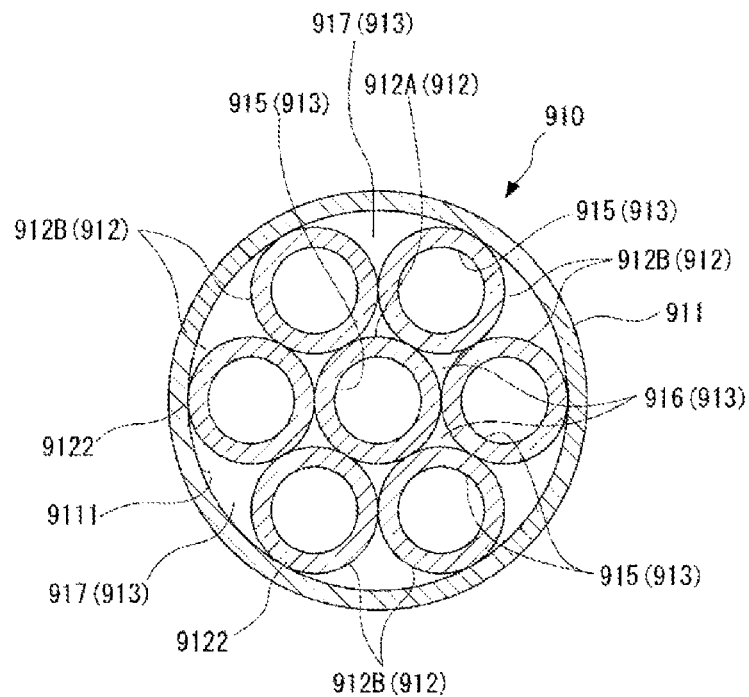
FIG. 14 is a sectional view of a flow passage member of a liquid collector according to an embodiment.

FIG. 14 illustrates a flow passage member 910 of a liquid collector according to an embodiment. Referring to FIG. 14, the flow passage member 910 includes an outer tube 911 and inner pipes 912.

The outer tube 911 has a tubular shape that extends in a pipe axis direction Ds connecting one end and other end of the flow passage member 910 (direction orthogonal to the plane of FIG. 14). In the embodiment of the present disclosure, the outer tube 911 has, for example, a circular shape in cross-section when viewed in the pipe axis direction Ds.

The inner pipes 912 are inserted in the outer tube 911. Each inner pipe 912 has a tubular shape that extends in the pipe axis direction Ds. Each inner pipe 912 has a uniform cross-sectional shape in the pipe axis direction Ds. In the embodiment of the present disclosure, each inner pipe 912 has, for example, a circular shape in cross-section when viewed in the pipe axis direction Ds. The inner pipes 912 have an outer diameter less than an inner diameter of the outer tube 911. The inner pipes 912 are inserted in the outer tube 911. An inner pipe 912A, which is one of the inner pipes 912, is disposed at the center of the outer tube 911. Inner pipes 912B, which are the remaining ones of the inner pipes 912, are arranged in contact with each other in the circumferential direction in a region radially outside the inner pipe 912A. Each inner pipe 912 extends continuously in the pipe axis direction Ds. Each inner pipe 912 has a hole 915 that extends therethrough in the pipe axis direction Ds. In some embodiments, each single pipe may have a cross-sectional shape that varies in the pipe axis direction. For example, each single pipe may be a combination of two single pipes having different sizes (for example, hole diameters).

A plurality of gaps 916 are formed between the inner pipe 912A and the inner pipes 912B arranged radially outside the inner pipe 912A. Each gap 916 extends continuously in the pipe axis direction Ds to connect the one end and the other end of the flow passage member 910.

The inner pipes 912B inserted in the outer tube 911 have outer peripheral surfaces 9122 that are in contact with, or slightly spaced from, an inner peripheral surface 9111 of the outer tube 911. In the flow passage member 910, the inner peripheral surface 9111 of the outer tube 911 and the outer peripheral surfaces 9122 of two of the inner pipes 912B that are adjacent to each other in the circumferential direction define an outer peripheral gap 917 therebetween. The outer peripheral gap 917 continuously extends in the pipe axis direction Ds to connect one end and the other end of the flow passage member 910.

Thus, the holes 915, the gaps 916, and the outer peripheral gaps 917 are defined in the flow passage member 910. The holes 915, the gaps 916, and the outer peripheral gaps 917 each serve as a flow passage 913 for the liquid in the flow passage member 910. The flow passage member 910 has a plurality of flow passages 913 (holes 915, gaps 916, and outer peripheral gaps 917). The flow passages 913 extend in the pipe axis direction Ds connecting the one end and the other end of the flow passage member 910. The flow passages 913 are substantially parallel to each other.

In some embodiments, the above-described flow passage member 910 may be used instead of the flow passage members 110, 210, 310, 410, and 510.

Figure 15:
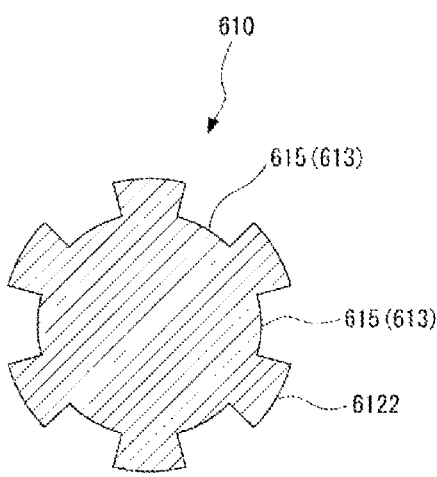
FIG. 15 is a sectional view of a flow passage member of a liquid collector according to an embodiment.

FIG. 15 illustrates a flow passage member 610 of a liquid collector according to an embodiment. Referring to FIG. 15, the flow passage member 610 has a columnar shape that extends in a pipe axis direction Ds connecting one end and other end of the flow passage member 610 (direction orthogonal to the plane of FIG. 15). The flow passage member 610 has a uniform cross-sectional shape in the pipe axis direction Ds. The flow passage member 610 has a plurality of grooves 615. The grooves 615 are arranged with equal intervals therebetween in a circumferential direction around a central axis of the flow passage member 610. Each groove 615 is recessed radially inward from an outer peripheral surface 6122 of the flow passage member 610. Each groove 615 extends continuously in the pipe axis direction Ds.

Each groove 615 serves as a flow passage 613 for the liquid in the flow passage member 610. The flow passage member 610 includes a plurality of flow passages 613 (grooves 615). The flow passages 613 extend in the pipe axis direction Ds connecting the one end and the other end of the flow passage member 610. The flow passages 613 are substantially parallel to each other.

In some embodiments, the above-described flow passage member 610 may be used instead of the flow passage members 110, 210, 310, 410, and 510.

Figure 16:
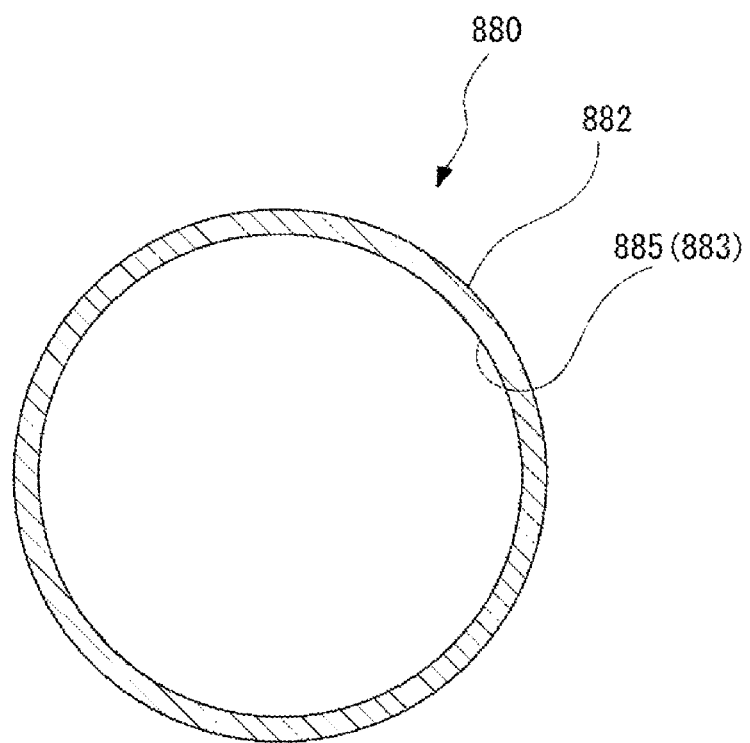
FIG. 16 is a sectional view of a flow passage member of a liquid collector according to an embodiment.

FIG. 16 illustrates a flow passage member 880 of a liquid collector according to an embodiment. As illustrated in FIG. 16, the flow passage member 880 includes one pipe 882.

The pipe 882 has a tubular shape that extends in a pipe axis direction Ds (direction orthogonal to the plane of FIG. 16). The pipe 882 has a uniform cross-sectional shape in the pipe axis direction Ds. In the embodiment of the present disclosure, the pipe 882 has, for example, a circular shape in cross-section when viewed in the pipe axis direction Ds. The pipe 882 may also have, for example, an elliptical shape in cross-section when viewed in the pipe axis direction Ds. The pipe 882 may also have, for example, a polygonal shape, such as a triangular shape, a quadrangular shape, a pentagonal shape, a hexagonal shape, or an octagonal shape in cross-section when viewed in the pipe axis direction Ds. The pipe 882 has a hole 885 that extends therethrough in the pipe axis direction Ds.

The hole 885 serves as a flow passage 883 for the liquid in the flow passage member 880. The flow passage member 880 includes the flow passage 883 (hole 885). The flow passage 883 extends in the pipe axis direction Ds connecting one end and other end of the flow passage member 880.

In some embodiments, the above-described flow passage member 880 may be used instead of the flow passage members 110, 210, 310, 410, and 510.

The present disclosure also provides the following embodiments:

A001

A liquid collector that collects liquid, the liquid collector including:
- a flow passage member including a flow passage that connects one end and other end of the flow passage member;
- a contact member that is disposed at the one end of the flow passage member, that includes an elastic material, and that is configured to come into contact with a target from which liquid is to be collected; and
- a container that receives the liquid discharged from the flow passage at the other end of the flow passage member.

A101

The liquid collector according to Embodiment A001, wherein the flow passage member includes a plurality of the flow passages that extend in a pipe axis direction connecting the one end and the other end of the flow passage member.

A102

The liquid collector according to Embodiment A101, wherein the plurality of the flow passages are substantially parallel to each other.

A103

The liquid collector according to Embodiment A101 or A102, wherein the flow passage member has a columnar shape that extends in the pipe axis direction connecting the one end and the other end of the flow passage member, and has a plurality of grooves that extend in the pipe axis direction along an outer peripheral surface of the flow passage member.

A104

The liquid collector according to Embodiment A101 or A102, wherein the flow passage member includes
- an outside tube having a tubular shape that extends in the pipe axis direction, and
- an inside member inserted in the outside tube and having a plurality of grooves that extend in the pipe axis direction along an outer peripheral surface of the flow passage member, and wherein an inner peripheral surface of the outside tube and the plurality of grooves in the inside member define the plurality of the flow passages.

A105

The liquid collector according to Embodiment A101 or A102, wherein the flow passage member has a columnar shape that extends in the pipe axis direction, and the plurality of the flow passages extend through the flow passage member in the pipe axis direction to provide communication between the one end and the other end of the flow passage member.

A106

The liquid collector according to Embodiment A101 or A102, wherein the flow passage member includes a plurality of single pipes that are bundled together and that extend in the pipe axis direction.

A107

The liquid collector according to Embodiment A101 or A102, wherein the flow passage member includes
- an outer tube having a tubular shape that extends in the pipe axis direction, and
- a plurality of inner pipes that are inserted in the outer tube and that extend in the pipe axis direction.

A111

The liquid collector according to any one of Embodiments A001 to A107, wherein the container includes
- a peripheral wall having a tubular shape that extends in the pipe axis direction, and
- a bottom portion that blocks the peripheral wall at one side in the pipe axis direction.

A112

The liquid collector according to Embodiment A111, wherein the bottom portion of the container is spaced from the other end of the flow passage member in the pipe axis direction, and wherein a reservoir space that stores the liquid is defined between the bottom portion of the container and the other end of the flow passage member.

A113

The liquid collector according to Embodiment A111 or A112,
- wherein the peripheral wall of the container has an inner diameter that gradually decreases toward the bottom portion in the pipe axis direction.

A114

The liquid collector according to any one of Embodiments A111 to A113,
- wherein the other end of the flow passage member is in contact with an inner peripheral surface of the peripheral wall of the container.

A115

The liquid collector according to any one of Embodiments A111 to A114,
- wherein the container has an air hole that provides communication with an outside of the container.

A116

The liquid collector according to any one of Embodiments A111 to A115,
- wherein the container has a scale mark that indicates an amount of the liquid received in the

A121

The liquid collector according to any one of Embodiments A101 to A115, further including:
- a cone-shaped portion disposed in the container, wherein at least a portion of the cone-shaped portion in the pipe axis direction has an inner diameter that gradually decreases toward the bottom portion in the pipe axis direction.

A122

The liquid collector according to Embodiment A121,
- wherein the other end of the flow passage member is in contact with an inner peripheral surface of the cone-shaped portion.

A131

The liquid collector according to any one of Embodiments A001 to A122,
- wherein the contact member includes
  - an inlet opening that comes into contact with a surface of the target from which the liquid is to be collected and allows introduction of the liquid that is on or near the surface, and
  - an outlet opening that is connected to the inlet opening to provide fluid communication and also connected to the flow passage member to provide fluid communication.

A132

The liquid collector according to Embodiment A131,
- wherein the one end of the flow passage member is fitted to the outlet opening of the contact member.

A133

The liquid collector according to Embodiment A132,
- wherein the contact member includes a sleeve that has a tubular shape and extends toward the other end of the flow passage member.

A134

The liquid collector according to any one of Embodiments A131 to A133,
- wherein the contact member has a contact surface in a region around the inlet opening, the contact surface coming into contact with the surface of the target from which the liquid is to be collected.

A135

The liquid collector according to Embodiment A134,
- wherein at least a portion of the contact surface is spherical.

A136

The liquid collector according to any one of Embodiments A101 to A135,
- wherein the container has an opening at a side opposite to a side at which the bottom portion is provided in the pipe axis direction, and
- wherein the contact member is disposed to close the opening.

A002

A liquid collector that collects liquid, the liquid collector including:
- a flow passage member including a plurality of flow passages that connect one end and other end of the flow passage member; and
- a container that receives the liquid discharged from the plurality of flow passages at the other end of the flow passage member.

A201

The liquid collector according to Embodiment A002, further including:
- a cone-shaped portion disposed in the container, wherein at least a portion of the cone-shaped portion in the pipe axis direction has an inner diameter that gradually decreases toward the bottom portion in the pipe axis direction.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

REFERENCE SIGNS LIST

100 liquid collector
110 flow passage member
111 outside tube
112 inside member
113 flow passage
113$d$ flow passage
120 contact member
121 flow-passage-member receiving hole
123 contact surface
130 container
131 peripheral wall
132 bottom portion
133 opening
138 reservoir space
139 scale mark
200 liquid collector 210 flow passage member
211 outside tube
212 inside member
213 flow passage
213d flow passage
220 contact member
221 flow-passage-member receiving hole
223 contact surface
230 container
231 peripheral wall
232 bottom portion
233 opening
238 reservoir space
239 scale mark
300 liquid collector
310 flow passage member
311 outside tube
312 inside member
313 flow passage
320 contact member
321 flow-passage-member receiving hole
323 contact surface
330 container
331 peripheral wall
332 bottom portion
333 opening
338 reservoir space
339 scale mark
340 inner member
341 cone-shaped portion
400 liquid collector
410 flow passage member
411 outside tube
412 inside member
413 flow passage
420 contact member
421 flow-passage-member receiving hole
423 contact surface
425 sleeve
430 container
431 peripheral wall
432 bottom portion
433 opening
438 reservoir space
439 scale mark
440 inner member
441 cone-shaped portion
500 liquid collector
510 flow passage member
511 outside tube
512 inside member
513 flow passage
530 container
531 peripheral wall
532 bottom portion
533 opening
538 reservoir space
539 scale mark
540 inner member
541 cone-shaped portion
610 flow passage member
613 flow passage
615 groove
710 flow passage member
713 flow passage
715 through hole
715A through hole
715B through hole
810 flow passage member
812 single pipe
812A single pipe
812B single pipe
813 flow passage
815 hole
816 gap
880 flow passage member
882 pipe
883 flow passage
885 hole
910 flow passage member
911 outer tube
912 inner pipe
912A inner pipe
912B inner pipe
913 flow passage
915 hole
916 gap
917 outer peripheral gap
999 liquid
1000 surface
1101 one end
1102 other end
1111 inner peripheral surface
1121 groove
1122 outer peripheral surface
1211 inlet opening
1212 outlet opening
2101 one end
2102 other end
2111 inner peripheral surface
2121 groove
2122 outer peripheral surface
2211 inlet opening
2212 outlet opening
2314 inner peripheral surface
3101 one end
3102 other end
3111 inner peripheral surface
3121 groove
3122 outer peripheral surface
3211 inlet opening
3212 outlet opening
3411 first opening
3412 second opening
4101 one end
4102 other end
4111 inner peripheral surface
4121 groove
4122 outer peripheral surface
4211 inlet opening
4212 outlet opening
4411 first opening
4412 second opening
5101 one end
5102 other end
5111 inner peripheral surface
5121 groove
5122 outer peripheral surface
5411 first opening
5412 second opening
6122 outer peripheral surface
9111 inner peripheral surface 9122 outer peripheral surface
Ds pipe axis direction
Dv vertical direction

The invention claimed is:

1. A liquid collector for collecting liquid, the liquid collector comprising:
a flow channel member including a flow channel that connects one end and other end of the flow channel member;
a contact member disposed at the one end of the flow channel member, and that includes an elastic material; and the contact member comprising:
an inlet opening configured to come into contact with a surface of the target from which the liquid is to be collected and to allow introduction of the liquid that is on or near the surface, and
an outlet opening connected to the inlet opening to provide fluid communication and also connected to the flow channel member to provide fluid communication, wherein the one end of the flow channel member is fitted to the outlet opening of the contact member;
a container configured to receive the liquid discharged from the flow channel at the other end of the flow channel member; and
a cone-shaped portion disposed in the container, wherein at least a portion of the cone-shaped portion in the pipe axis direction has an inner diameter that decreases toward a bottom portion in the pipe axis direction,
wherein the other end of the flow channel member is in contact with an inner peripheral surface of the cone-shaped portion.

2. The liquid collector according to claim 1,
wherein the contact member includes a sleeve that has a tubular shape and extends toward the other end of the flow channel member.

3. The liquid collector according to claim 1,
wherein the contact member has a contact surface in a region around the inlet opening, the contact surface coming into contact with the surface of the target from which the liquid is to be collected.

4. The liquid collector according to claim 3,
wherein at least a portion of the contact surface is spherical.

5. The liquid collector according to claim 1,
wherein the flow channel member includes a plurality of the flow channels that extend in a pipe axis direction connecting the one end and the other end of the flow channel member.

6. The liquid collector according to claim 5,
wherein the plurality of the flow channels are substantially parallel to each other.

7. The liquid collector according to claim 5,
wherein the flow channel member has a columnar shape that extends in the pipe axis direction connecting the one end and the other end of the flow channel member, and has a plurality of grooves that extend in the pipe axis direction along an outer peripheral surface of the flow channel member.

8. The liquid collector according to claim 5,
wherein the flow channel member includes
an outside tube having a tubular shape that extends in the pipe axis direction, and
an inside member inserted in the outside tube and having a plurality of grooves that extend in the pipe axis direction along an outer peripheral surface of the flow channel member, and
wherein an inner peripheral surface of the outside tube and the plurality of grooves in the inside member define the plurality of the flow channels.

9. The liquid collector according to claim 5, wherein
the flow channel member has a columnar shape that extends in the pipe axis direction, and the plurality of the flow channels extend through the flow channel member in the pipe axis direction to provide communication between the one end and the other end of the flow channel member.

10. The liquid collector according to claim 5,
wherein the flow channel member includes a plurality of single pipes that are bundled together and that extend in the pipe axis direction.

11. The liquid collector according to claim 5,
wherein the flow channel member includes:
an outer tube having a tubular shape that extends in the pipe axis direction, and
a plurality of inner pipes that are inserted in the outer tube and that extend in the pipe axis direction.

12. The liquid collector according to claim 5,
wherein the container has an opening at a side opposite to a side at which the bottom portion is provided in the pipe axis direction, and
wherein the contact member is disposed to close the opening.

13. The liquid collector according to claim 1,
wherein the container includes:
a peripheral wall having a tubular shape that extends in the pipe axis direction, and
a bottom portion that blocks the peripheral wall at one side in the pipe axis direction.

14. The liquid collector according claim 13,
wherein the bottom portion of the container is spaced from the other end of the flow channel member in the pipe axis direction, and
wherein a reservoir space to store the liquid is defined between the bottom portion of the container and the other end of the flow channel member.

15. The liquid collector according claim 13,
wherein the peripheral wall of the container has an inner diameter that gradually decreases toward the bottom portion in the pipe axis direction.

16. The liquid collector according to claim 13,
wherein the other end of the flow channel member is in contact with an inner peripheral surface of the peripheral wall of the container.

17. The liquid collector according to claim 13,
wherein the container has an air hole that provides communication with an outside of the container.

18. The liquid collector according to claim 13,
wherein the container has a scale mark to indicate an amount of the liquid received in the container.

* * * * *